United States Patent [19]

Harada et al.

[11] 4,233,237
[45] Nov. 11, 1980

[54] 2-ALKOXYALKOXY-5-AMINOBENZENE-SULFONIC ACID

[75] Inventors: Tooru Harada; Shinsaku Fujita, both of Minami-ashigara, Japan

[73] Assignee: Fuji Photo Film Co., Ltd., Minami-ashigara, Japan

[21] Appl. No.: 13,752

[22] Filed: Feb. 21, 1979

[30] Foreign Application Priority Data

Feb. 20, 1978 [JP] Japan ................................. 53-18373

[51] Int. Cl.³ .......................................... C07C 143/64
[52] U.S. Cl. .................................... 260/509; 260/152
[58] Field of Search ......................................... 260/509

[56] References Cited

FOREIGN PATENT DOCUMENTS 1416574 12/1975 United Kingdom ..................... 260/509

OTHER PUBLICATIONS

Research Disclosure, vol. 130, No. 13024, (1975).

Primary Examiner—Nicky Chan
Attorney, Agent, or Firm—Sughure, Rothwell, Mion, Zinn and Macpeak

[57] ABSTRACT

A 2-alkoxyalkoxy-5-aminobenzenesulfonic acid represented by the following general formula (I):

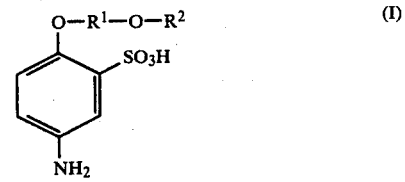

wherein $R^1$ represents an alkylene group having 2 or more carbon atoms; and $R^2$ represents an alkyl group. The compound can be used as an intermediate in the production of a dye releasing redox compound.

9 Claims, 4 Drawing Figures

2-ALKOXYALKOXY-5-AMINOBENZENESULFONIC ACID

BACKGROUND OF THE INVENTION

1. Field of the Invention

The present invention relates to a compound useful as an intermediate in the preparation of a dye releasing redox compound which is suitable for use in the color diffusion transfer process and, more particularly, to a compound useful as an intermediate for producing a dye releasing redox compound having improved transferability, light fastness and hue.

2. Description of the Prior Art

Color diffusion transfer color image forming processes using a dye releasing redox compound are described in Japanese Patent Application (OPI) No. 104343/1976 (The term "OPI" as used herein refers to a "published unexamined Japanese patent application"), U.S. Pat. Nos. 3,932,381, 3,943,987, 3,928,312, 3,931,144 and 3,954,476, and Research Disclosure, No. 13024 (1975). The term "dye releasing redox compound" refers to a compound in which a group referred to as the "redox moiety" and a dye (including a dye precursor) moiety are bonded. The redox moiety has attached thereto a ballast group which renders the redox compound immobile, but the redox moiety splits from the compound and releases a compound having a dye moiety upon redox reaction with the oxidized color developing agent under alkaline condition. That is, a light-sensitive element comprising a light-sensitive silver halide emulsion layer having associated therewith a redox compound is exposed to light and developed with an alkaline processing solution, whereby the redox compound per se is oxidized in proportion to the amount of developed silver halide and the compound splits into a compound having a dye moiety (hereinafter referred to as the "dye compound") and a non-diffusible quinone compound by means of the alkaline processing solution. As a result, the dye compound diffuses into an image receiving layer to provide a transferred image therein.

Examples of redox compounds which release yellow dyes are described in U.S. Pat. No. 3,928,312 and Research Disclosure, 13024 (1975). However, technical problems are accompanied using the dye releasing redox compound as specifically described in these publications. The stability of the transferred color images is not sufficient (for example, the light fastness of the images is not good and the color images fade to a large extent under light) and the transfer of dye compounds is not sufficient and the transfer speed of dye compounds is low.

In addition, improved yellow dye releasing redox compounds are described in U.S. Pat. No. 4,013,633. However, as a result of recent investigations, it has been learned that these redox compounds suffer a change in hue of the dye compounds depending on the pH of the system.

Examples of redox compounds which release magenta dyes are described in U.S. Pat. Nos. 3,932,380 and 3,931,144. However, using such dye releasing redox compounds as specifically described in these publications, technical problems are encountered. The stability of transferred color images is insufficient (for example, the light fastness of the color images is not good and the color images fade to a large extent under light) and the transfer of the dye compounds is not sufficient.

With respect to the fading-in-dark of transferred magenta dye images, it has been known that unreacted monomer (such as acrylic acid, butyl acrylate, etc.), when a polymer acid (for example, polyacrylic acid, a copolymer of acrylic acid and butyl acrylate, etc.) as disclosed in U.S. Pat. No. 3,362,819 is used for a neutralization layer, adversely influences the fading-in-dark of transferred dye images. It has also been found upon further investigations that unreacted butyl acrylate monomer, in particular, increases the fading-in-dark of the magenta dye image obtained from a method as described in the prior art, for example, U.S. Pat. No. 3,932,380. However, it is extremely difficult from a technical standpoint to limit the amount of unreacted monomer to such an extent that it does not adversely influence the light fastness of the image. Therefore, it has been desired to develop a redox compound which releases a dye compound which is less sensitive to such unreacted acid monomer.

SUMMARY OF THE INVENTION

A principal object of the present invention is to provide a compound useful as an intermediate for producing dye releasing redox compounds which provide stable yellow and magenta dye images.

A second object of the present invention is to provide a compound useful as an intermediate for producing yellow and magenta dye releasing redox compounds having a dye moiety which when released has excellent color hue.

Another object of the present invention is to provide a compound useful as an intermediate for producing dye releasing redox compounds which provides transferred yellow and magenta dye images which are not subject to a change in hue with pH.

Still another object of the present invention is to provide a compound useful as an intermediate for producing a dye releasing redox compound which releases a dye compound having improved transferability.

The above-described objects are accomplished with a 2-alkoxyalkoxy-5-aminobenzenesulfonic acid represented by the following general formula (I):

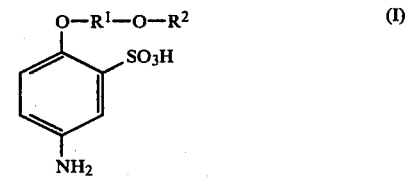

wherein $R^1$ represents an alkylene group having 2 or more carbon atoms and $R^2$ represents a substituted or unsubstituted alkyl group.

BRIEF DESCRIPTION OF THE DRAWINGS

FIG. 1 is the infrared spectrum of the sodium salt of 2-(2-methoxy-ethoxy)-5-aminobenzenesulfonate.

FIG. 2 is the infrared spectrum of 2-(2-methoxy-ethoxy)-5-aminobenzenesulfonic acid.

FIG. 3 is the infrared spectrum of 2-(2-ethoxy-ethoxy)-5-aminobenzenesulfonic acid.

FIG. 4 is the infrared spectrum of 2-(2-propoxyethoxy)-5-aminobenzenesulfonic acid.

DETAILED DESCRIPTION OF THE INVENTION

Figure 1:
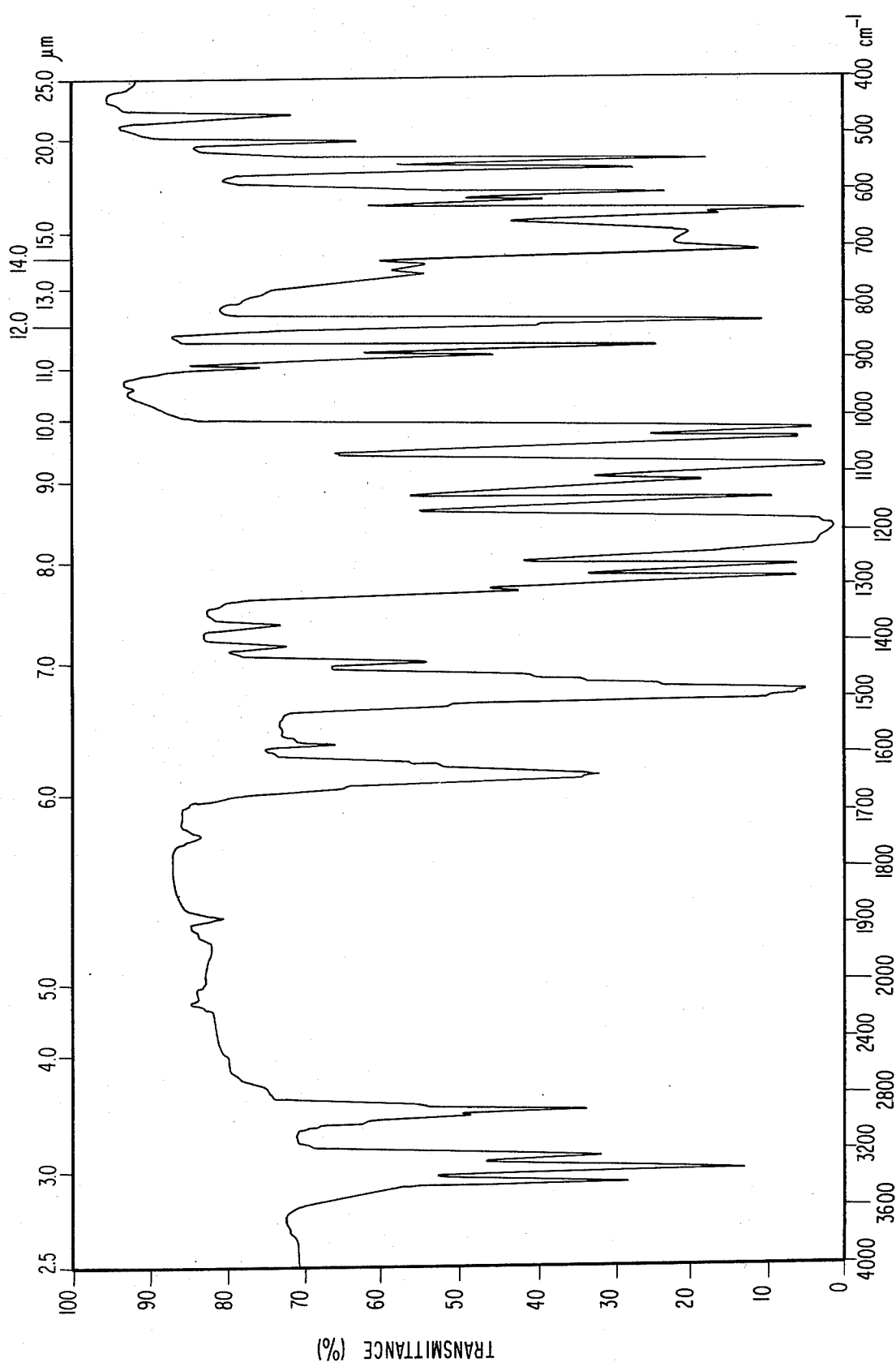
FIGS. 1 to 4 are the infrared absorption spectra of compounds of the present invention.

In more detail, the alkylene group having 2 or more carbon atoms represented by $R^1$ can be a straight chain or branched chain alkylene group. An alkylene group having 2 to 8 carbon atoms is preferred. Branched chain alkylene groups which form an acetal linkage (the term "acetal linkage" as used herein means two oxygen atoms in the $-O-R^1-OR^2$ moiety connected to the same carbon atom in the $R^1$ moiety) are excluded. Particularly preferred examples of $R^1$ are a straight chain alkylene group, $-(CH_2)_p-$, wherein p is an integer of 2 to 4, and a branched chain alkylene group having 3 or 4 carbon atoms, e.g., a $-CH(CH_3)CH_2-$ group and a $-CH_2CH_2CH(CH_3)-$ group, an alkylene group which forms an acetal linkage being excluded. From the standpoint of the availability of the starting material, it is particularly advantageous for $R^1$ to be $-CH_2CH_2-$. If $R^1$ were to be a methylene group, it would form an acetal linkage, such as $-O-CH_2-O-R^2$ which is chemically unstable, particularly under acidic conditions, and tends to decompose during preparation. For the same reason, it is also undesirable for the two oxygen atoms to be bonded to the same carbon atom in the $-O-R^1-O-R^2$ group, and for this reason the formation of an acetal linkage is excluded.

The alkyl group represented by $R^2$ can be a straight chain or branched chain alkyl group and preferably is an alkyl group having 1 to 8 carbon atoms. The term "alkyl group" as used with respect to $R^2$ in formula (I) includes both substituted and unsubstituted alkyl groups, however, from the standpoint of the preparation of the compound, $R^2$ is preferably an unsubstituted alkyl group. A particularly preferred example of the alkyl group for $R^2$ is a straight chain or branched chain alkyl group having 1 to 4 carbon atoms (for example, a methyl group, an ethyl group, an n-propyl group, an isopropyl group, an n-butyl group, etc.). From the standpoint of the preparation of the compound, a straight chain alkyl group having 1 to 4 carbon atoms, particularly a methyl group and an ethyl group, are particularly preferred for $R^2$.

In summary, particularly preferred compounds according to the present invention are those in which $R^1$ represents a $-CH_2CH_2-$ group and $R^2$ represents a straight chain or branched chain alkyl group having 1 to 4 carbon atoms. More preferred are compounds in which $R^1$ represents a $-CH_2CH_2-$ group and $R^2$ represents a straight chain alkyl group having 1 to 4 carbon atoms. Even more preferred are compounds in which $R^1$ represents a $-CH_2CH_2-$ group and $R^2$ represents a methyl group and an ethyl group.

Specific examples of the compounds according to the present invention are shown below.

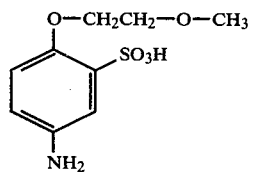

Compound (1a)

-continued

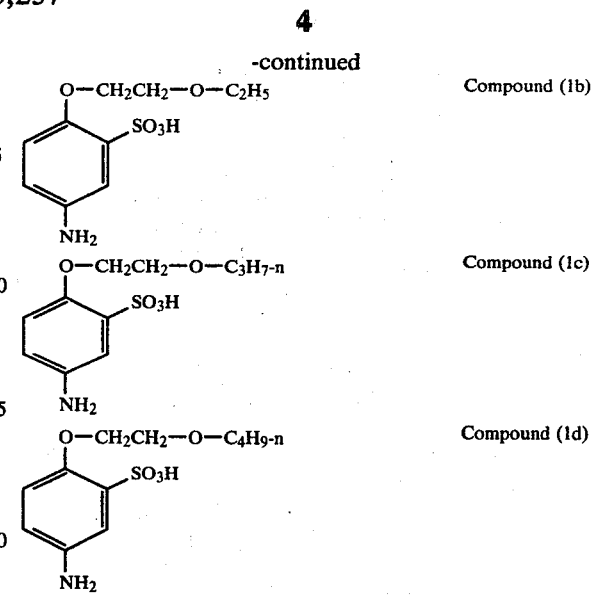

Compound (1b)

Compound (1c)

Compound (1d)

An example of a method for preparing the compounds of the present invention is illustrated by the chemical equation below.

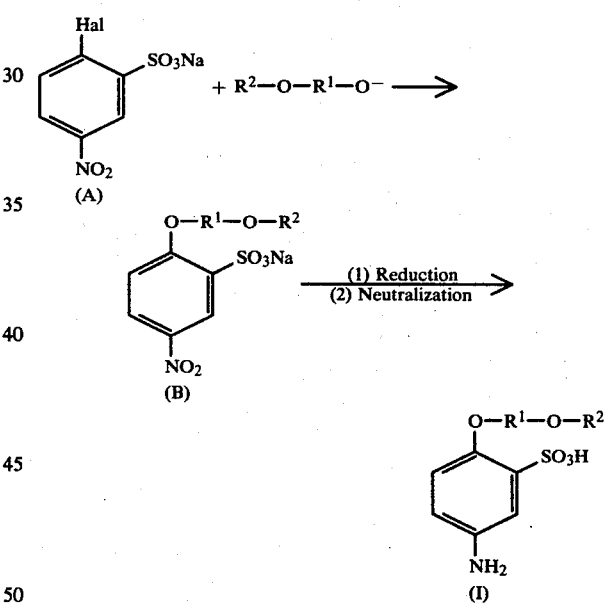

In the above equation, Hal represents a halogen atom and preferably a chlorine atom and $R^1$ and $R^2$ each has the same meaning as defined in the general formula (I).

One method for preparing Compound (B) comprises reacting Compound (A) with an alkoxide represented by the general formula:

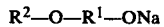

$$R^2-O-R^1-ONa$$

wherein $R^1$ and $R^2$ each has the same meaning as defined in the general formula (I). The alkoxide is obtained by treating an alcohol of the formula $R^2-O-R^1-OH$ with metallic sodium hydride. While the alkoxide of the formula $R^2-O-R^1-ONa$ can be isolated by distilling off the excess alcohol, usually a solution of $R^2-O-R^1-ONa$ in $R^2-O-R^1-OH$ is used. The alkoxide is used in amounts of from about 1 mol to about 50 mols, preferably from about 1 mol to about 10 mols, and more preferably from about 1 mol to about 3 mols, per mol of Compound (A). A suitable temperature for the reaction of Compound (A) with the alkoxide ranges from about −20° C. to about 150° C., preferably from 0° C. to 100° C., and more preferably from 30° C. to 85° C. in order to minimize the formation of by-products.

Another method for preparing Compound (B) comprises reacting Compound (A) in $R^2$—O—$R^1$—OH in the presence of sodium hydroxide or potassium hydroxide in the presence of manganese dioxide. Sodium hydroxide is preferably used in this method. More particularly, 1 mol of Compound (A) and from about 10 g to about 1 kg, preferably from about 10 g to about 500 g, more preferably from about 30 g to about 100 g, of manganese dioxide are suspended in from about 100 ml to about 50 l, preferably from about 300 ml to about 5 l, more preferably from about 400 ml to about 2 l, of $R^2$—O—$R^1$—OH and then treated with from about 1 mol to about 50 mols, preferably from about 1 mol to about 10 mols, more preferably from about 1 mol to about 3 mols, of sodium hydroxide. In this method, the reaction temperature is desirably maintained at from about 0° C. to about 150° C., preferably from 0° C. to 100° C., more preferably from 30° C. to 85° C.

A third method for preparing Compound (B) comprises treating Compound (A) in $R^2$—O—$R^1$—OH with sodium hydroxide or potassium hydroxide in the presence of sodium silicate ($Na_2O.nSiO_2$ wherein n is from about 1 to about 5, preferably from about 1 to about 3). Sodium hydroxide is preferably used in this method. More particularly, 1 mol of Compound (A) and from about 10 g to about 1,000 g, preferably from about 10 g to about 500 g, more preferably from about 30 g to about 100 g, of sodium silicate are suspended in from about 100 ml to about 50 l, preferably from about 300 ml to about 5 l, more preferably from about 400 ml to about 2 l, of the alcohol $R^2$—O—$R^1$—OH and then treated with from about 1 mol to about 50 mols, preferably from about 1 mol to about 10 mols, more preferably from about 1 mol to about 3 mols, of sodium hydroxide. In this method, the reaction temperature is desirably maintained at from about 0° C. to about 150° C., preferably at from 0° C. to 100° C., more preferably at from 30° C. to 85° C.

A reaction solution obtained in any one of the above-described methods is filtered to remove insoluble substances. The filtrate is poured into a poor solvent (for example, an alcohol solvent such as isopropyl alcohol, n-butanol, etc.; an aromatic hydrocarbon solvent such as toluene, etc.; an ester solvent such as ethyl acetate, etc.) to crystallize Compound (B). Conventional purification procedures such as recrystallization can additionally be conducted, if desired.

In addition, Compound (B) can be obtained by sulfonation of a compound of the formula:

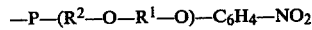

in a manner similar to that described in Chemical Abstracts Vol. 52 4536b. Further it is possible to chlorosulfonate a compound of the formula:

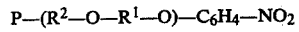

using chlorosulfonic acid. In this case, it is believed that the compound is obtained through the sulfonic acid (Na is substituted with H in formula (B)). L. F. Fieser, *Experiments in Organic Chemistry*, 3rd Ed., Chapter 26, D. C. Heath and Co. (1955), describes general methods for obtaining a sulfonyl chloride using chlorosulfonic acid. By refluxing a sulfonylchloride (i.e., 2-alkoxyalkoxy-5-nitrobenzenesulfonyl chloride) in methanol, a methanol solution of the corresponding sulfonic acid (wherein Na is substituted with H in the formula (B)) is obtained. By treating the compound thus-prepared with potassium acetate, calcium hydroxide, barium hydroxide, pyridine, etc., a compound in which Na is substituted with $K^+$, $Ca_{\frac{1}{2}}{}^{+2}$, $Ba_{\frac{1}{2}}{}^{+2}$ or $C_5H_6N^+$, etc., in formula (B) is obtained, respectively. A calcium salt and a barium salt can also be prepared using the difference in solubility in water, etc., from a corresponding sodium salt.

These derivatives of the Compound (B) are useful as intermediates in the synthesis of the compound of the general formula (I). However, from the standpoint of the costs of preparation and the like, it is preferred to simply employ pre-synthesized Compound (B) as an intermediate.

As the methods for reducing the nitro group of the Compound (B) to obtain Compound (I), reduction with iron dust, catalytic hydrogenation (Raney nickel or palladium-carbon or active carbon catalyst) are typical. Conventional methods for reducing a nitro group to an amino group can be used as described in, for example, R. B. Wagner et H. D. Zook, *Synthetic Organic Chemistry*, Chap. 24, pp. 654–657 (John Wiley, New York, (1953)), S. R. Sandler et W. Karo, *Organic Functional Group Preparations*, Chap. 13, pp. 339–345 (Academic Press, London, (1968)), and the like. These methods are also effective for synthesizing compounds of the present invention.

The method for reducing the nitro group of Compound (B) to obtain Compound (I) will be described in more detail using iron dust as an example. About 1 mol to 100 mols, preferably about 1 mol to about 50 mols, more preferably about 1 mol to 10 mols, of iron dust (iron powder or the like being preferable) is used per 1 mol of Compound (B). As the solvent for the reduction reaction, water or alcohol (e.g., methanol, ethanol, methoxyethanol, etc.) is preferable. It is also possible to use these solvents in combination. Further, ammonium chloride is desirably added as a reaction initiator in a small amount (about 1/100 to about 1/10, preferably about 1/100 to about 1/20, of the weight of the compound of general formula (B)). The temperature of the above-described reaction is desirably maintained at about 30° C. to about 150° C., preferably about 50° C. to about 100° C. The thus-obtained reaction solution is filtered to remove insolubles and, upon pouring the filtrate into a poor solvent (e.g., isopropyl alcohol), the sodium salt of the compound of the general formula (I) is precipitated. Also, when the filtered reaction solution described above is neutralized with conc. hydrochloric acid, the compound of the general formula (I) can be obtained as an inner salt.

Typical synthesis examples of the Compound (B) are illustrated in detail below.

SYNTHESIS EXAMPLE 1

Sodium 2-(2-Methoxyethoxy)-5-nitrobenzenesulfonate, Compound Ba

Method 1:

To a solution of sodium 2-methoxyethylate prepared by adding 7.3 g of sodium hydride (14.6 g of a 50% suspension in liquid paraffin) to 300 ml of 2-methoxyethanol, was added 55 g of sodium 2-chloro-5-nitrobenzenesulfonate with stirring. The reaction mixture was heated at 80° to 85° C. on a water bath while stirring for 30 minutes. After filtering the mixture while hot, 1.5 liters of isopropyl alcohol was added to the filtrate to form crystals. The crystals thus-precipitated were recovered by filtration and washed with 100 ml of isopropyl alcohol. Yield: 59%. Melting Point: 238° to 239° C.

Method 2

A mixture of 5.2 g of sodium 2-chloro-5-nitrobenzenesulfonate, 0.6 g of manganese dioxide, 15 ml of 2-methoxyethanol, 1 ml of water and 0.95 g of sodium hydroxide was stirred at 75° C. for 40 minutes. After cooling, the insoluble materials were removed by filtration and the filtrate was poured into 100 ml of isopropyl alcohol. The crystals thus-precipitated were recovered by filtration to obtain 4.8 g of sodium 2-(2-methoxyethoxy)-5-nitrobenzenesulfonate. Melting Point: 238° to 239° C. The compound obtained by Method 2 was the same as that obtained by Method 1.

Method 3

Using procedures identical to those described in Method 2 above except that 0.8 g of sodium silicate ($Na_2O \cdot nSiO_2$ wherein n is about 3) was used in place of the manganese dioxide, 4.8 g of sodium 2-(2-methoxyethoxy)-5-nitrobenzenesulfonate was obtained. The same results were obtained using $Na_2O \cdot nSiO_2$ wherein n is about 1, about 2 and about 2.5, respectively. The compound obtained in Method 3 was the same as the compound obtained in Methods 1 and 2.

SYNTHESIS EXAMPLE 2

Sodium 2-(2-Ethoxyethoxy)-5-nitrobenzenesulfonate, Compound Bb

To a solution of sodium 2-ethoxyethylate prepared by adding 7.3 g of sodium hydride (14.6 g of a 50% suspension in liquid paraffin) to 300 ml 2-ethoxyethanol, was added 55 g of sodium 2-chloro-5-nitrobenzenesulfonate. The reaction mixture was heated at 80° to 85° C. with stirring for 30 minutes. After completion of the reaction, the insoluble materials were removed by filtration and from the filtrate 150 ml of ethyl Cellosolve was distilled under reduced pressure. To the concentrated solution was added 300 ml of isopropyl alcohol and the mixture was cooled with ice. The crystals thus-precipitated were recovered by filtration, washed with 100 ml of isopropyl alcohol and air-dried. Yield: 33 g. Melting Point: 248° to 249° C.

Compound Bb could also be obtained using 2-ethoxyethanol in place of 2-methoxyethanol in Method 2 or Method 3 of Synthesis Example 1.

SYNTHESIS EXAMPLE 3

Sodium 2-(2-Propoxyethoxy)-5-nitrobenzenesulfonate, Compound Bc 26.0 g of sodium 2-chloro-5-nitrobenzenesulfonate and 5.0 g of sodium silicate ($Na_2O \cdot nSiO_2$ wherein n is about 3) were suspended in 120 ml of 2-propoxyethanol. To the suspension was added dropwise with stirring a solution containing 5.0 g of sodium hydroxide dissolved in 5 ml of water at 65° C. for 10 minutes. After completion of the addition, the reaction mixture was stirred at 65° C. for 3 hours and the insoluble materials were removed by filtration under suction. The solids which deposited from the filtrate upon standing were removed by filtration. The filtrate was concentrated to a dry solid. 100 ml of ethanol was added to the residue to form crystals. The crystals were recovered by filtration, washed with isopropyl alcohol and dried at 50° C. Yield: 14.1 g. The compound at first melted at 70° to 74° C., then solidified at about 130° C. and again melted at 206° to 209° C.

SYNTHESIS EXAMPLE 4

Sodium 2-(2-Butoxyethoxy)-5-nitrobenzenesulfonate, Compound Bd

The above-described compound was obtained in the same manner as described in Method 2 of Synthesis Example 1 except that ethylene glycol monobutyl ether was used in place of 2-methoxyethanol. Melting Point: 104° to 106° C.

Specific examples of the synthesis of the sodium salt of the compound of the present invention are illustrated in detail below.

SYNTHESIS EXAMPLE 5

Synthesis of the corresponding sodium salt of Compound 1a

A mixture solution of 30 g of sodium 2-(2-methoxyethoxy)-5-nitrobenzenesulfonate, Compound Ba, obtained in Synthesis Example 1, 30 g of reduced iron, 0.6 g of ammonium chloride and 60 ml of water was heated at 80° to 85° C. with stirring for 2 hours. After completion of the reaction, the insoluble materials were removed by filtration, 200 ml of isopropyl alcohol was added to the filtrate and the mixture was cooled with ice. The crystals thus-precipitated were collected by filtration, washed with 50 ml of isopropyl alcohol and air-dried. Yield: 23 g. Melting Point: above 250° C.

| Elemental Analysis | | | |
|---|---|---|---|
| | H | C | N |
| Calcd. for $C_9H_{12}NO_5SNa$ (%): | 4.49 | 40.15 | 5.20 |
| Found (%): | 4.44 | 39.87 | 5.22 |

The infrared absorption spectrum of this compound (KBr tablet method) is shown in FIG. 1.

SYNTHESIS EXAMPLE 6

Synthesis of Compound 1a

A mixed solution of 20 g of sodium 2-(2-methoxyethoxy)-5-nitrobenzenesulfonate monohydrate, Compound Ba, obtained in Synthesis Example 1, 10 g of reduced iron, 0.4 g of ammonium chloride, 40 ml of isopropyl alcohol and 40 ml of water was stirred for 90 minutes at 77° C. After completion of the reaction, insolubles were removed by filtration, and 20 ml of concentrated hydrochloric acid (36%) was added to the filtrate. Crystals thus-formed were collected by filtration, washed with 50 ml of isopropyl alcohol, and air-dried. Yield: 19.6 g. Melting Point: 286°–289° C.

| Elemental Analysis | | | |
|---|---|---|---|
| | H | C | N |
| Calcd. for $C_9H_{15}NO_6S$ (%): | 5.70 | 40.74 | 5.28 |
| Found (%): | 5.50 | 41.02 | 5.18 |

Figure 2:
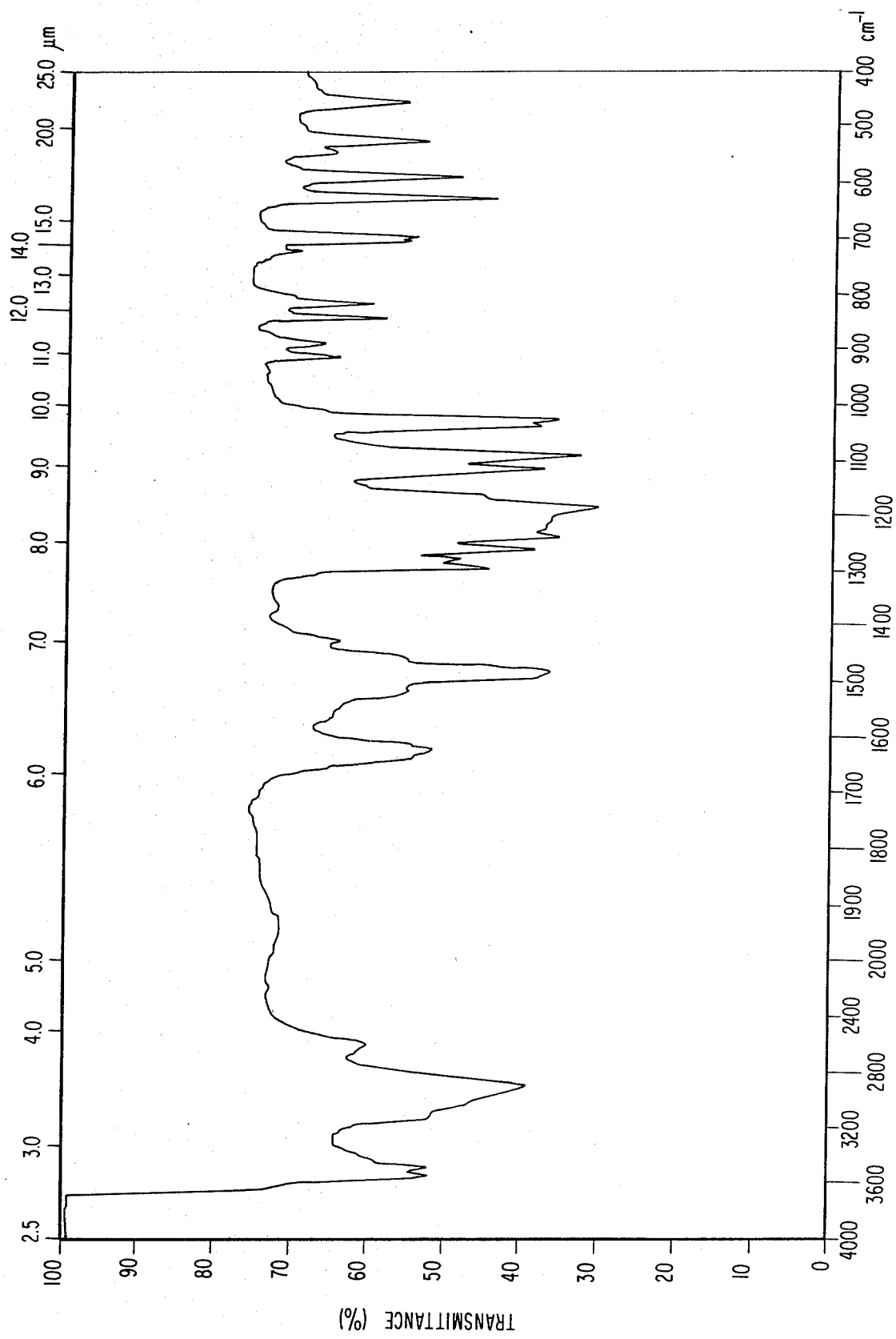

The infrared absorption spectrum of this compound (KBr tablet method) is shown in FIG. 2.

SYNTHESIS EXAMPLE 7

Synthesis of Compound 1b

A mixture solution of 10 g of sodium 2-(2-ethoxyethoxy)-5-nitrobenzenesulfonate, Compound Bb, obtained in Synthesis Example 2, 5 g of reduced iron, 0.2 g of ammonium chloride, 20 ml of isopropyl alcohol and 20 ml of water was stirred for 2 hours at 77° C. After completion of the reaction, insoluble materials were removed by filtration, and 10 ml of concentrated hydrochloric acid (36%) was added to the filtrate. Crystals thus-formed were collected by filtration, washed with 30 ml of isopropyl alcohol, and air-dried. Yield: 7.6 g. Melting Point: 278°-283° C.

| Elemental Analysis | H | C | N |
|---|---|---|---|
| Calcd. for $C_{10}H_{15}NO_5S$ (%): | 5.79 | 45.97 | 5.36 |
| Found (%): | 5.73 | 45.86 | 5.24 |

Figure 3:
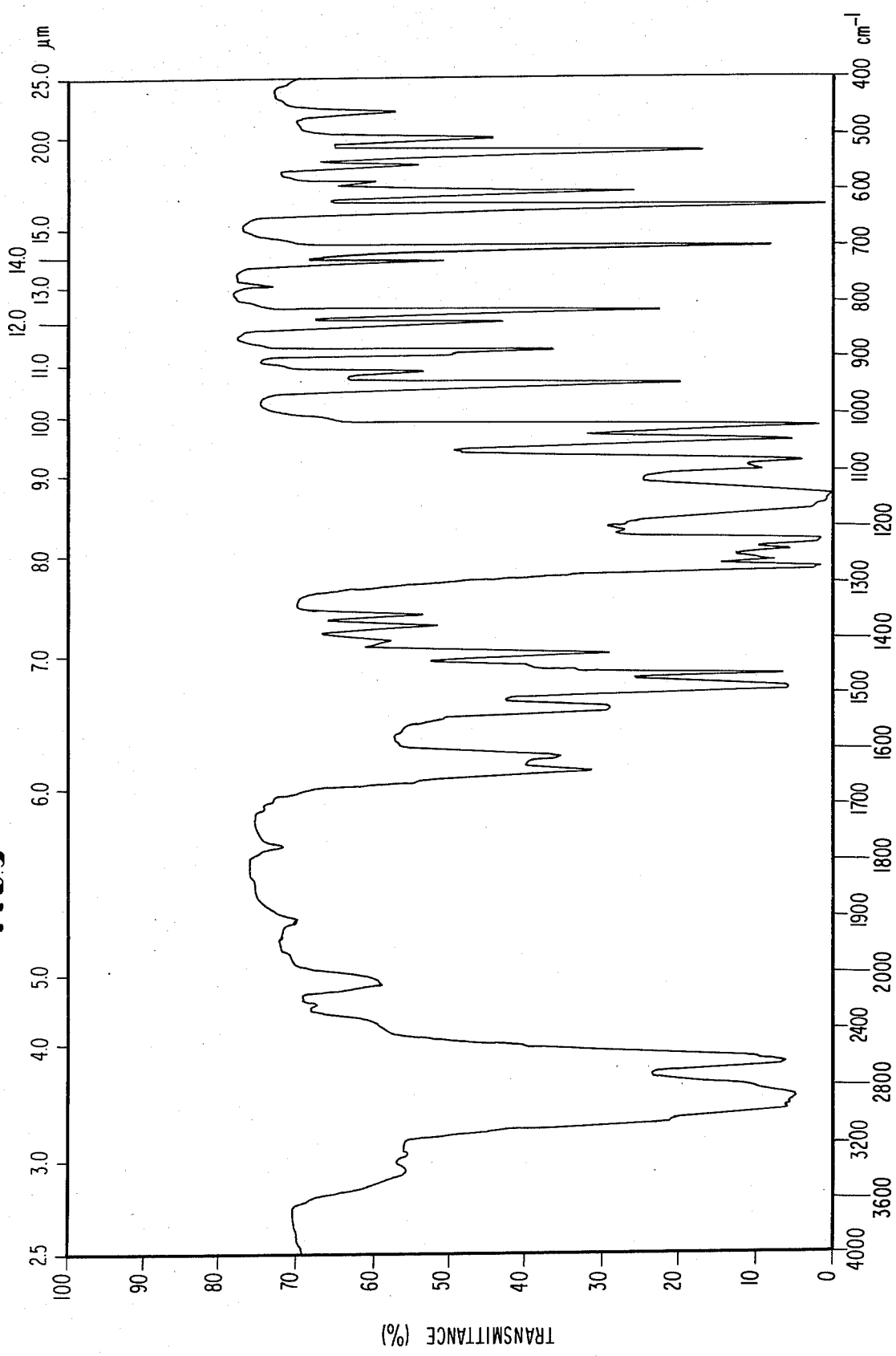

The infrared absorption spectrum of this compound (KBr tablet method) is shown in FIG. 3.

SYNTHESIS EXAMPLE 8

Synthesis of Compound 1c

A mixture solution of 10 g of sodium 2-(2-propoxyethoxy)-5-nitrobenzenesulfonate, Compound Bc, 5 g of reduced iron, 0.2 g of ammonium chloride, 20 ml of isopropyl alcohol and 20 ml of water was stirred at 77° C. for 2 hours. After completion of the reaction, insoluble materials were removed by filtration, and 10 ml of concentrated hydrochloric acid (36%) was added to the filtrate. Crystals thus-formed were collected by filtration, and air-dried. Yield: 7.1 g. Melting Point: 287°-290° C.

| Elemental Analysis | H | C | N |
|---|---|---|---|
| Calcd. for $C_{11}H_{17}NO_5S$ (%): | 6.22 | 47.99 | 5.09 |
| Found (%): | 6.11 | 47.41 | 4.99 |

Figure 4:
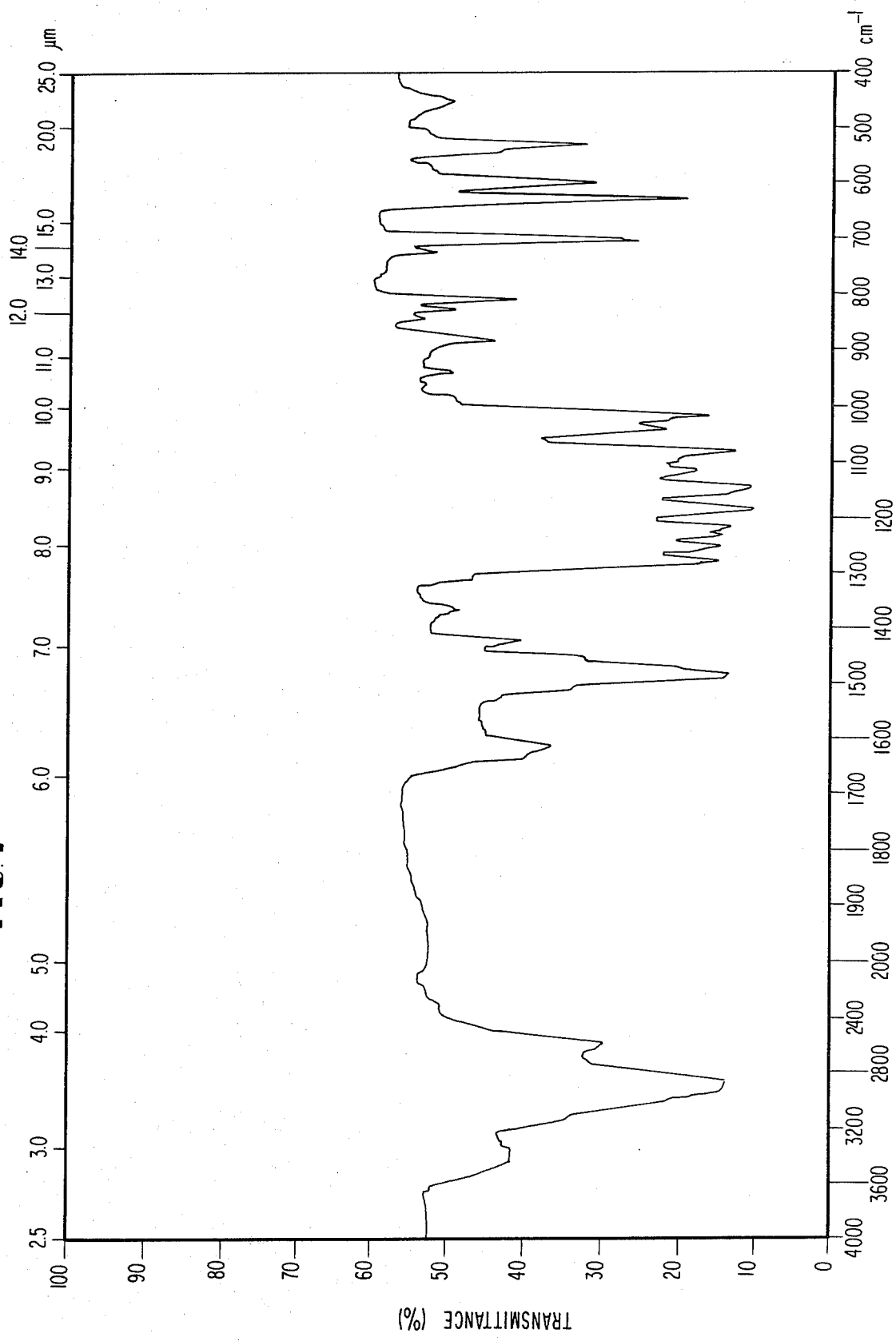

The infrared absorption spectrum of this compound (KBr tablet method) is shown in FIG. 4.

By using the compound of the present invention as an intermediate, a dye releasing redox (DRR) compound which is suitable for use in color diffusion transfer process can be prepared. The DRR compounds and their synthesis are the subject of currently copending and commonly assigned applications Ser. No. 956,698, filed Nov. 1, 1978 and Ser. No. 13,998 corresponding to Japanese Patent Application No. 18372/1978, filed on even date with this application, which are incorporated herein by reference. For convenience, however, the DRR compounds and their synthesis are set forth below.

Typical examples of these DRR compounds include compounds represented by the following general formula (II):

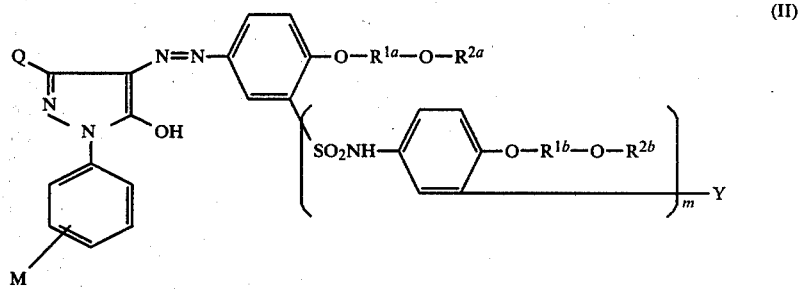

wherein Q represents a cyano group, a trifluoromethyl group, a carbamoyl group represented by the formula $-CONR^3R^4$ wherein $R^3$ represents a hydrogen atom, an alkyl group or a substituted alkyl group; $R^4$ represents a hydrogen atom, an alkyl group, a substituted alkyl group, an aralkyl group, or an aryl group, and $R^3$ and $R^4$ can be combined directly or through an oxygen atom to form a ring; M represents a hydrogen atom, an alkyl group, a substituted alkyl group, a sulfamoyl group represented by the formula $-SO_2NR^3R^4$, wherein $R^3$ and $R^4$ each has the same meaning as defined above; a group represented by the formula $-COOR^5$, wherein $R^5$ represents an alkyl group, a substituted alkyl group, a phenyl group, or a substituted phenyl group; or a halogen atom; $R^{1a}$ and $R^{1b}$ which may be the same or different, have the same definition as $R^1$ and each represents an alkylene group having 2 or more carbon atoms; $R^{2a}$ and $R^{2b}$ which may be the same or different have the same definition as $R^2$ and each represents an alkyl group or substituted alkyl group; m represents 0 or 1; and Y represents an o- or p-hydroxyarylsulfamoyl group having a ballast group bonded thereto.

In the description hereinafter, the terms $R^1$ and $R^2$ refer to $R^{1a}$ and $R^{1b}$ and $R^{2a}$ and $R^{2b}$, respectively, and are analogous to $R^1$ and $R^2$ in the intermediate of formula (I).

The compound of formula (II) is characterized by the presence of the $-O-R^1-R^2$ group in the dye moiety (more particularly, the moiety corresponding to the diazo component). The $-O-R^1-O-R^2$ group positioned at the 4-position to the azo group and the $-SO_2NH-$ group (which is a part of Y in formula (II) when m is 0) positioned at the 3-position to the azo group is another characteristic. It is hereinafter described in detail that these positional relationships provide an advantage in preventing a change in the color hue of the released dye compound due to pH. In addition, advantages are also the result of the $-O-R^1-O-R^2$ group and Y being positioned ortho to one another. It is believed that due to this structural feature the function of Y as a redox moiety is intensified and thus the dye compound is effectively released from the dye releasing redox compound resulting in improved transferability.

Examples of the substituents of the substituted alkyl group $R^2$ (including $R^{2a}$ and $R^{2b}$) are an alkoxy group (for example, a methoxy group, an ethoxy group, etc.), a dialkylamino group (for example, a diethylamino group, etc.), and the like.

In the carbamoyl group represented by the formula —CONR$^3$R$^4$ for Q, R$^3$ is preferably a hydrogen atom, an alkyl group having 1 to 8 carbon atoms (more preferably 1 to 4 carbon atoms), and a substituted alkyl group having 1 to 8 carbon atoms (more preferably 1 to 4 carbon atoms) in the alkyl moiety. R$^4$ is preferably a hydrogen atom, an alkyl group having 1 to 8 carbon atoms (more preferably 1 to 4 carbon atoms), a substituted alkyl group having 1 to 8 carbon atoms (more preferably 1 to 4 carbon atoms), a benzyl group, a phenyl group, and a substituted phenyl group having 6 to 9 carbon atoms. Also, R$^3$ and R$^4$ may be combined directly or through an oxygen atom to form a 5- or 6-membered ring.

The cases where (i) R$^3$ and R$^4$ each represents a hydrogen atom, and (ii) at least one of R$^3$ and R$^4$ represents a hydrogen atom and the other of R$^3$ and R$^4$ represents an alkyl group having 1 to 4 carbon atoms; are particularly preferred because of the readily available starting materials and the excellent transferability of the dye compound formed. In terms of the light-stability of the transferred dye compound, it is particularly preferred that Q be a cyano group.

The alkyl group and the substituted alkyl group represented by M are preferably an alkyl group and a substituted alkyl group having 1 to 8, more preferably 1 to 4, carbon atoms in the alkyl moiety. Examples of substituents on the substituted alkyl group include those groups as described in R$^3$ to R$^5$ below.

In the sulfamoyl group represented by the formula —SO$_2$NR$^3$R$^4$ for M, R$^3$ and R$^4$ are preferably the same as those defined in the aforementioned formula —CONR$^3$R$^4$.

Preferred examples of R$^5$ include an alkyl group having 1 to 8, more preferably 1 to 4, carbon atoms, a substituted alkyl group having 1 to 8, more preferably 1 to 4, carbon atoms in the alkyl moiety, a phenyl group, and a substituted phenyl group.

Examples of substituents on the substituted alkyl group for R$^3$ to R$^5$ described above include a cyano group, an alkoxy group, a hydroxy group, a carboxy group, a sulfo group and the like.

The halogen atom represented by M is preferably a chlorine atom.

Examples of the substituents on the substituted phenyl group for R$^4$ to R$^5$ include a hydroxy group, a halogen atom, a carboxy group, a sulfo group, a sulfamoyl group, an alkyl group, an alkoxy group, and the like.

A preferred sulfamoyl group substituted with an o- or p-hydroxyaryl group having a ballast group represented by Y in formula (II) is of the general formula (III):

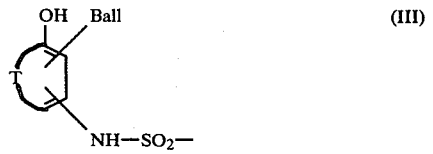

(III)

wherein Ball represents a ballast group, T represents an atomic group necessary to complete a benzene ring including a substituted benzene ring or a naphthalene ring including a substituted naphthalene ring; —NH-SO$_2$ group is present at o- or p-position to the hydroxy group; and when T represents a naphthalene ring, Ball may be bonded to either of the two naphthalene rings.

Examples of the substituents on the benzene ring or the naphthalene ring include, for example, an alkyl group, preferably are alkyl group having 1 to 7 carbon atoms, or a halogen atom (e.g., a chlorine atom, etc.).

The ballast group is an organic ballast group capable of rendering the dye releasing redox compound nondiffusible during development in an alkaline processing solution and preferably has a hydrophobic residue having 8 to 32 carbon atoms. Such an organic ballast group is bonded to the dye releasing redox compound directly or through a bridging group, for example, an imino bond, an ether bond, a thioether bond, a carbonamido bond, a sulfonamido bond, a ureido bond, an ester bond, an imido bond, a carbamoyl bond, a sulfamoyl bond, etc., alone or in combination.

Specific examples of ballast groups are illustrated below. An alkyl group or an alkenyl group (for example, a 2-ethylbutyl group, a dodecyl group, an octadecyl group, etc.), an alkoxyalkyl group (e.g., a 3-(octyloxy)propyl group, a 3-(2-ethylundecyloxy)propyl group, etc., as described in Japanese Patent Publication No. 27563/1964), an alkylaryl group (e.g., a 4-nonylphenyl group, a 2,4-di-tert-butylphenyl group, etc.), an alkylaryloxyalkyl group (for example, a 2,4-di-tert-pentylphenoxymethyl group, an α-(2,4-di-tert-pentylphenoxy)propyl group, a 1-(3-pentadecylphenoxy)ethyl group, etc.), an acylamidoalkyl group (e.g., a group described in U.S. Pat. Nos. 3,337,344 and 3,418,129, a 2-(N-butylhexadecanamido)ethyl group, etc.), an alkoxyaryl group (e.g., a 4-(n-octadecyloxy)phenyl group, a 4-(4-n-dodecylphenyloxy)phenyl group, etc.), a residue having both an alkyl or alkenyl long-chain aliphatic group and a water-solubilizing group such as a carboxy group or a sulfo group together (e.g., a 1-carboxymethyl-2-nonadecenyl group, a 1-sulfoheptadecyl group, etc.), an alkyl group substituted with an ester group (e.g., a 1-ethoxycarbonylheptadecyl group, a 2-(n-dodecyloxycarbonyl)ethyl group, etc.), an alkyl group substituted with an aryl group or a heterocyclic group (e.g., a 2-[4-(3-methoxycarbonyluneicosaneamido)-phenyl]ethyl group, a 2-[4-(2-n-octadecylsuccinimido)-phenyl]ethyl group, etc.), and an aryl group substituted with an aryloxy alkoxy carbonyl group (e.g., a 4-[2-(2,4-di-tert-pentylphenoxy)-2-methylpropyloxy carbonyl]-phenyl group, etc.).

Of the above-described organic ballast groups, those bonded to a bridging group as represented by the following general formulae are particularly preferred.

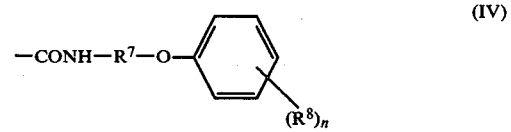

(IV)

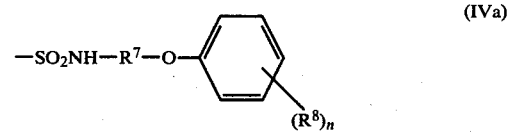

(IVa)

—CONH—R$^7$—O—R$^9$ (V)
—O—R$^{10}$ (VI)

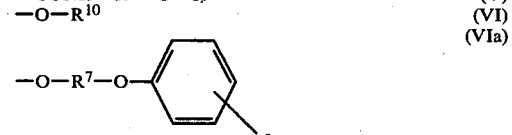

(VIa)

—O—R$^7$—O—CONH—R$^9$ (VIb)
—O—R$^7$—O—R$^9$ (VIc)
—CONHR$^9$ (VII)

wherein $R^7$ represents an alkylene group having 1 to 10 carbon atoms, preferably 1 to 6 carbon atoms (e.g., a propylene group, a butylene group, etc.) or an arylene group having 6 to 30 carbon atoms, preferably 6 to 20 carbon atoms (such as a phenylene group, etc.); $R^8$ represents a hydrogen atom or an alkyl group having 1 to 30 carbon atoms, preferably 1 to 20 carbon atoms (e.g., a tert-amyl group, a pentadecyl group, etc.); n represents an integer of 1 to 5 and preferably 1 or 2; $R^9$ represents an alkyl group having 4 to 30 carbon atoms, preferably 10 to 20 carbon atoms (e.g., a dodecyl group, a tetradecyl group, a hexadecyl group, etc.) or a group represented by the formula:

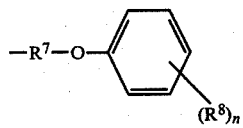

wherein $R^7$, $R^8$ and n have the same meaning as defined above (such as a 4-[(2,4-di-tert-amyl)phenyloxy]butyl group, etc.); and $R^{10}$ represents an alkyl group having 8 to 30 carbon atoms, preferably 10 to 20 carbon atoms (e.g., a hexadecyl group, an octadecyl group, etc.), or a substituted alkyl group having 8 or more total carbon atoms in which the alkyl moiety has 1 or more carbon atoms. Examples of the substituents are, for example, a carbamoyl group, an alkoxy group having 1 to 30 carbon atoms, preferably 1 to 20 carbon atoms (such as methoxy group, an ethoxy group, etc.), etc.

Specific examples of the sulfamoyl groups represented by formula (III) are illustrated below.

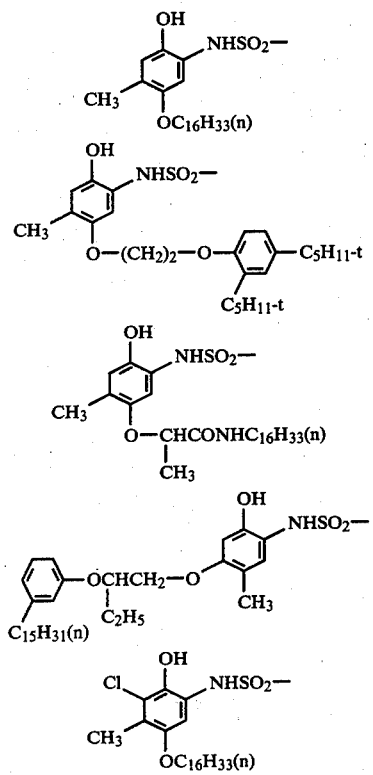

-continued

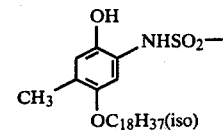

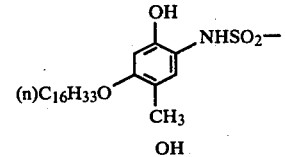

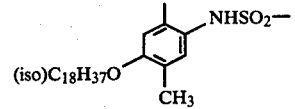

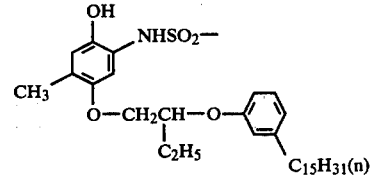

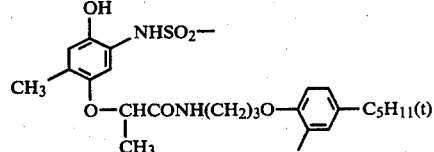

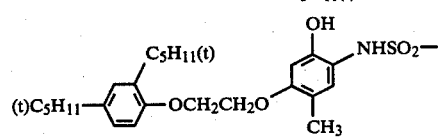

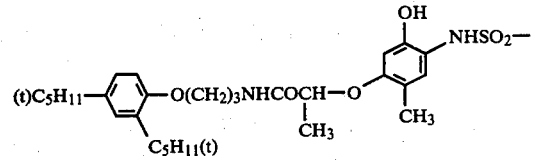

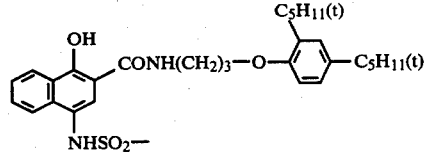

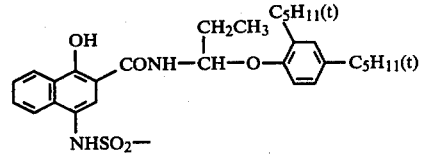

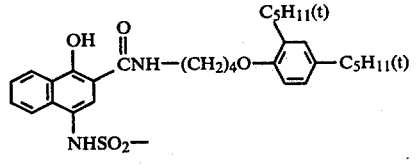

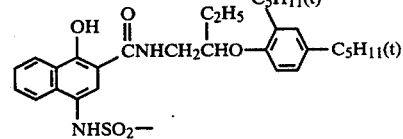

-continued

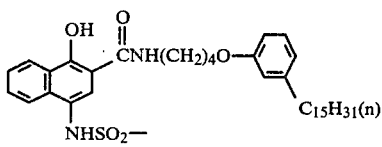

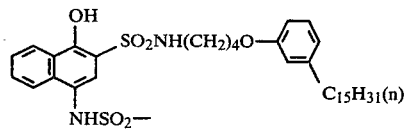

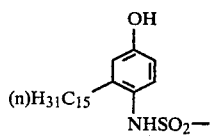

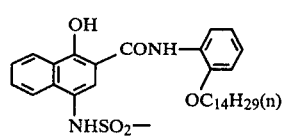

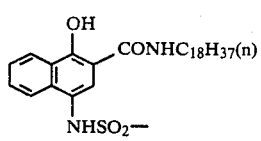

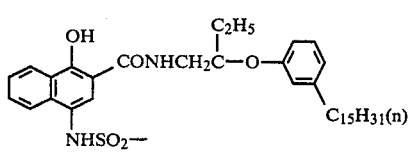

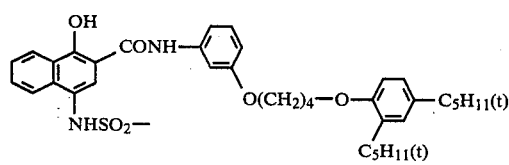

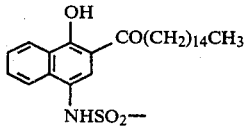

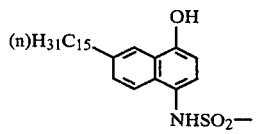

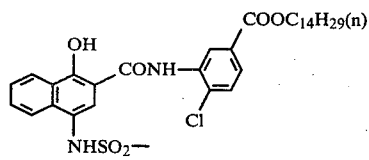

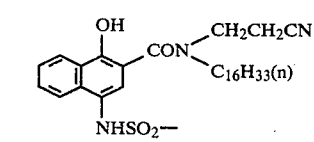

-continued

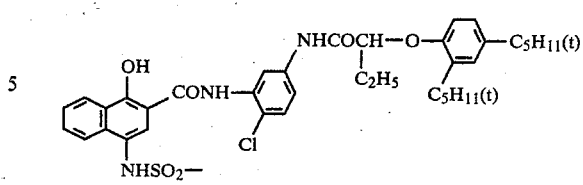

Furthermore, the groups described in *Research Disclosure*, Vol. 130, No. 13024 (February, 1975) are useful for Y.

A preferred compound which is obtained by using the intermediate according to the present invention is a compound represented by formula (II), in which $R^1$ represents —$CH_2CH_2$—; $R^2$ represents a straight chain or branched chain alkyl group having 1 to 4 carbon atoms (e.g., a methyl group, an ethyl group, an n-propyl group, an isopropyl group, an n-butyl group, etc.); Q represents a cyano group; M represents a hydrogen atom; m represents 0 or 1; and Y represents a sulfamoyl group represented by the general formula (III).

Particularly preferred DRR compounds are those represented by the above-described general formula (II) in which $R^1$ represents a —$CH_2CH_2$— group; $R^2$ represents a straight chain alkyl group having 1 to 4 carbon atoms; Q represents a cyano group; M represents a hydrogen atom; m is 0; and Y represents an o-hydroxyphenylsulfamoyl group having an alkyl group at the position meta to the hydroxy group in addition to a ballast group.

Specific examples of DRR compounds represented by the general formula (II) are shown below.

Compound II-1

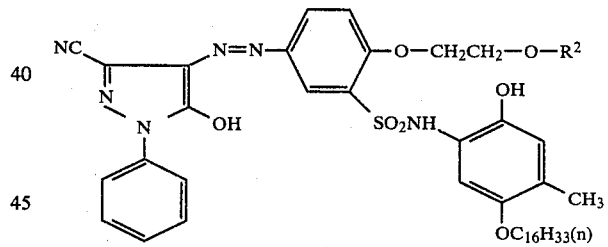

wherein $R^2$ is $CH_3$.
Compound II-2
$R^2$ is $C_2H_5$ in Compound II-1.
Compound II-3

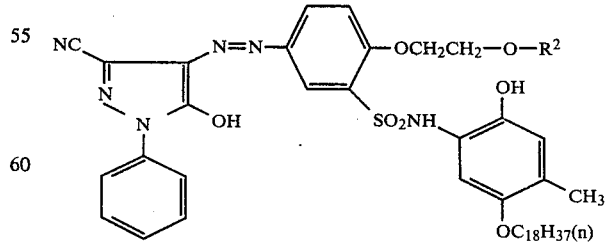

wherein $R^2$ is $CH_3$.
Compound II-4
$R^2$ is $C_2H_5$ in Compound II-3.
Compound II-5

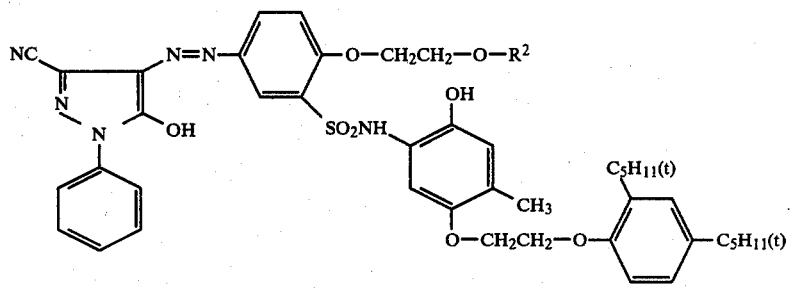
wherein R² is CH₃.
Compound II-6
R² is C₂H₅ in Compound II-7.
Compound II-9
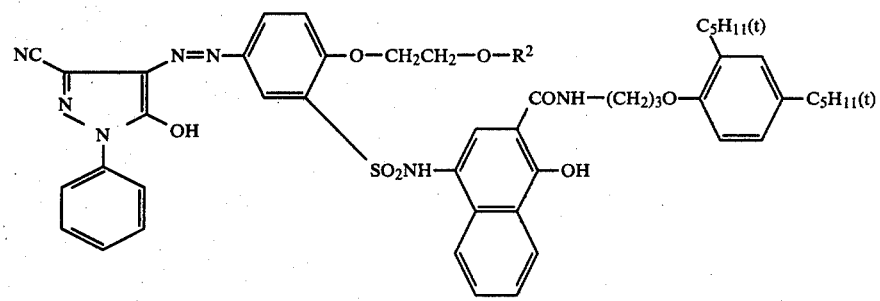
R² is CH₂CH₃ in Compound II-5.
Compound II-7
wherein R² is CH₃.
Compound II-10
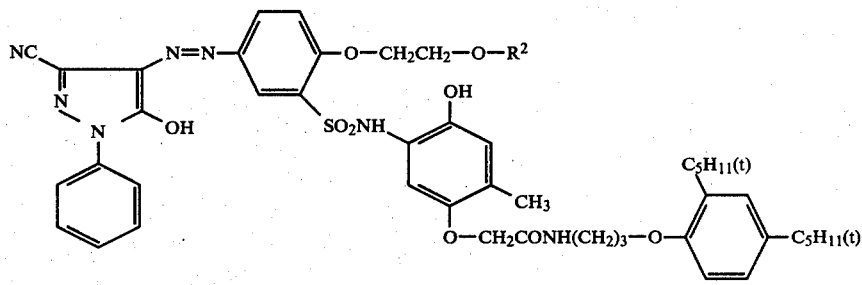
wherein R² is CH₃.
Compound II-8
R² is an ethyl group in Compound II-9.
Compound II-11
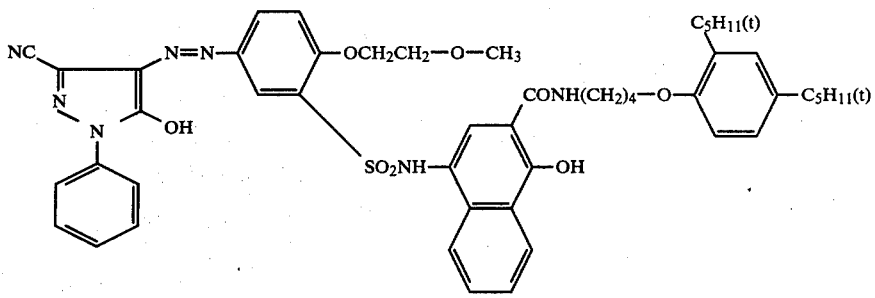
Compound II-12

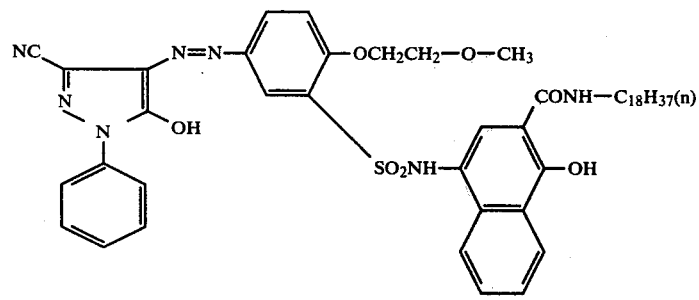
Compound II-13    wherein R² is CH₃.
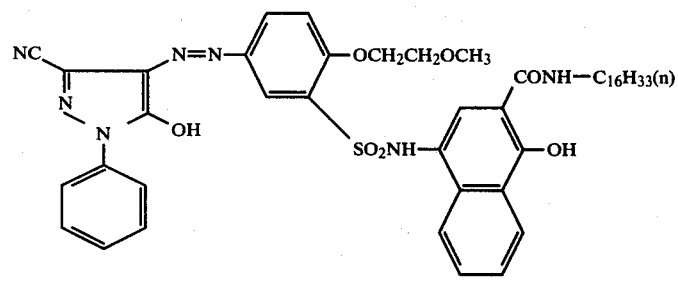
Compound II-14    Compound II-16
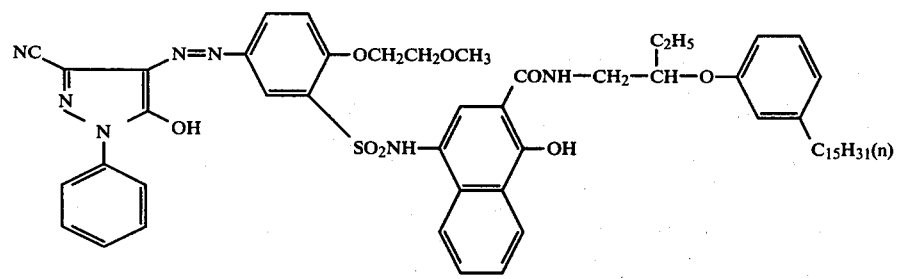
Compound II-15    R² is C₂H₅ in Compound II-15.
Compound II-17
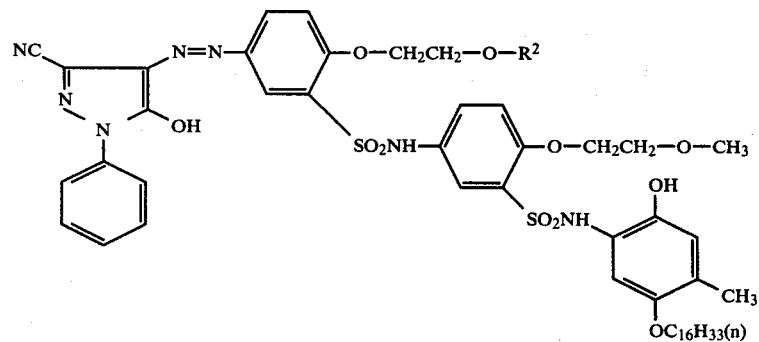

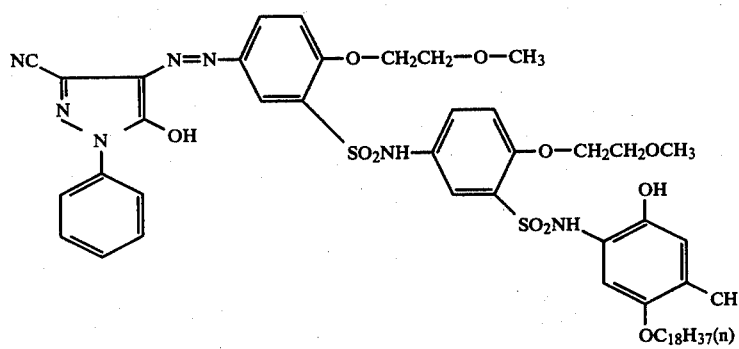
Compound II-18
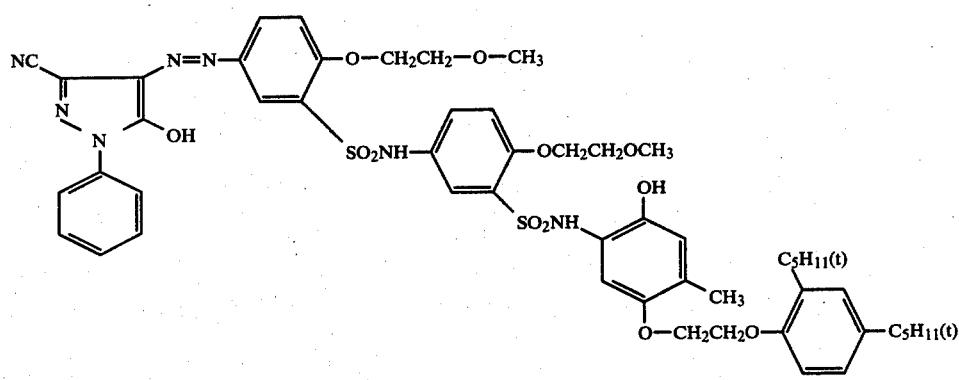
Compound II-20
Compound II-19
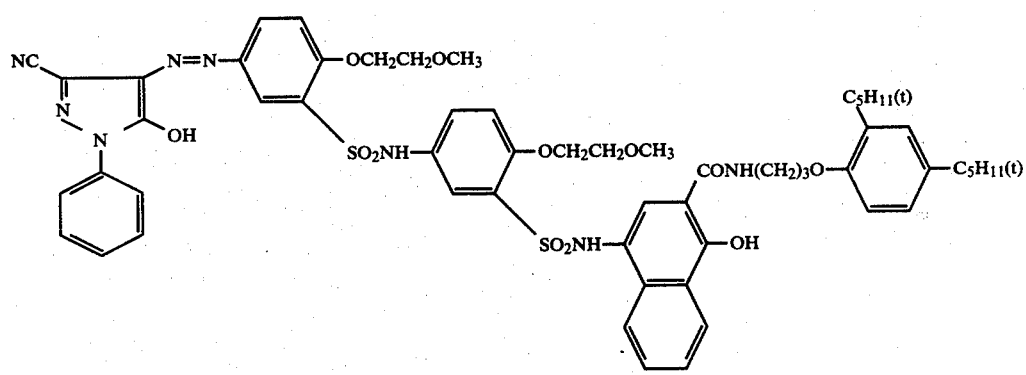
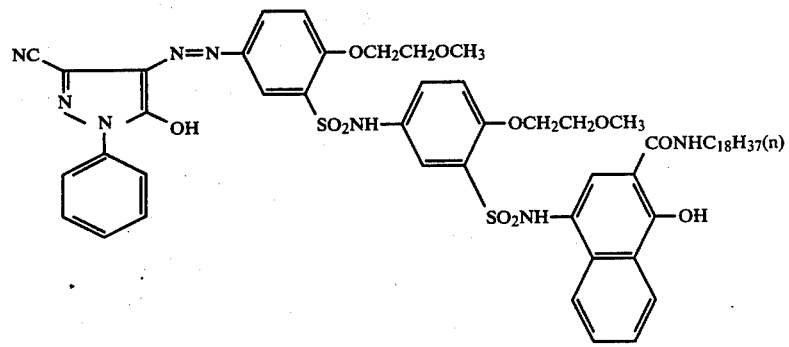

The compound of the general formula (II) releases a novel yellow dye compound represented by the following formula (VIII) or (IX):

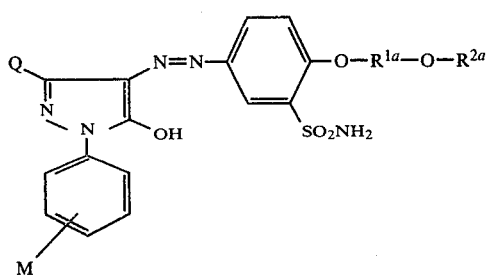

(VIII)

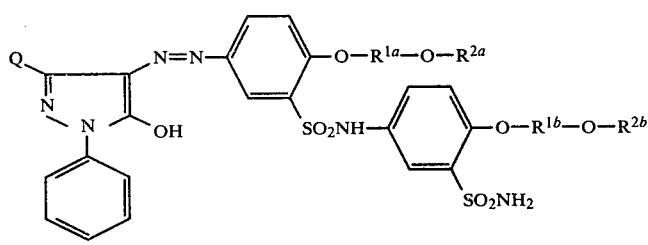

(IX)

wherein Q, M, $R^1$, $R^2$ each has the same meaning as defined in the general formula (II), when the compound is oxidized under alkaline conditions.

Other examples of DRR compounds synthesized using a compound of the present invention as an intermediate include compounds represented by the following general formula (X) (These compounds are the subject of Ser. No. 956,698, supra.)

formula (II); m represents 0 or 1; and Y has the same meaning as defined in the general formula (II).

Substituents on the substituted alkyl group represented by $R^6$ are preferably those described in $R^3$ to $R^5$ above.

Specific examples of DRR compounds derived from a compound of the present invention as an intermediate thereof are shown below.

Compound X-1

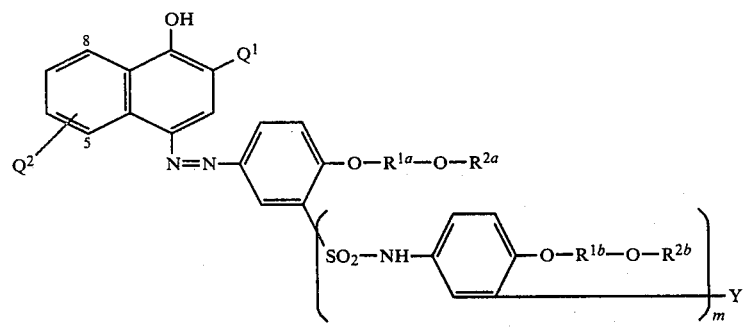

(X)

wherein $Q^1$ represents a hydrogen atom, a halogen atom, a sulfamoyl group represented by the formula of $-SO_2NR^3R^4$, wherein $R^3$ and $R^4$ each has the same meaning as defined in the general formula (II), a group represented by the formula of $-SO_2R^6$, wherein $R^6$ represents an alkyl group, a substituted alkyl group or a benzyl group, a carboxy group, a group represented by the formula of $-COOR^5$, wherein $R^5$ has the same meaning as defined in the general formula (II), or a group represented by the formula of $-CONR^3R^4$, wherein $R^3$ and $R^4$ each has the same meaning as defined in the general formula (II); $Q^2$, which is present at the 5- or 8-position to the hydroxy group of the naphthalene ring, represents a hydroxy group, or a group represented by the formula of $-NH-COR^4$ or $-NH-SO_2R^4$, wherein $R^4$ has the same meaning as defined in the general formula (II); $R^{1a}$ and $R^{1b}$ and $R^{2a}$ and $R^{2b}$ each has the same meaning as defined in the general

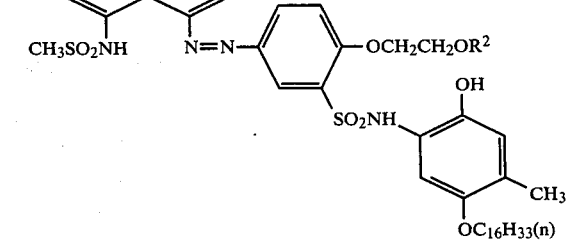

wherein $R^2$ is $CH_3$.

Compound X-2

$R^2$ is $C_2H_5$ in Compound X-1.

Compound X-3 wherein $R^3$ is hydrogen.
Compound X-5
   $R^3$ is $CH_3$ in Compound X-4.
Compound X-6
   $R^3$ is n-butyl in Compound X-4.
Compound X-7
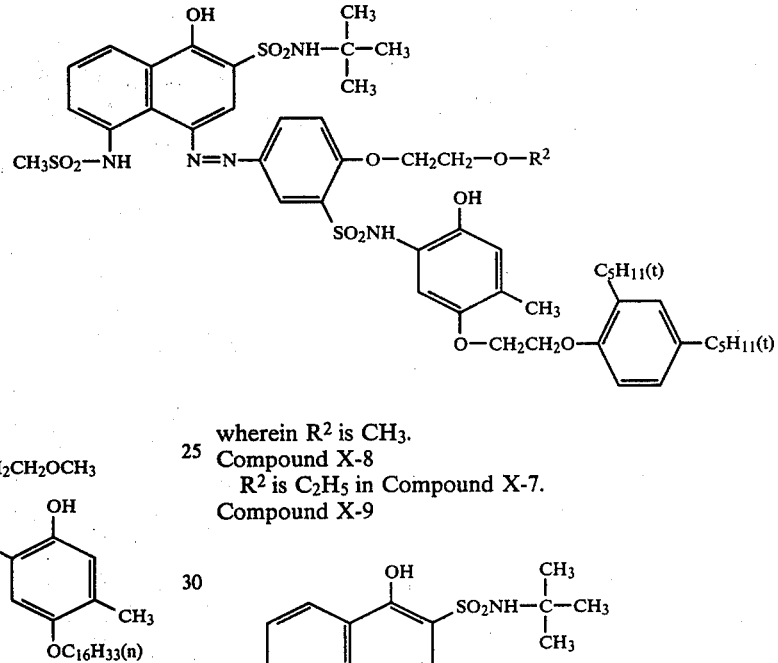
Compound X-4
wherein $R^2$ is $CH_3$.
Compound X-8
   $R^2$ is $C_2H_5$ in Compound X-7.
Compound X-9
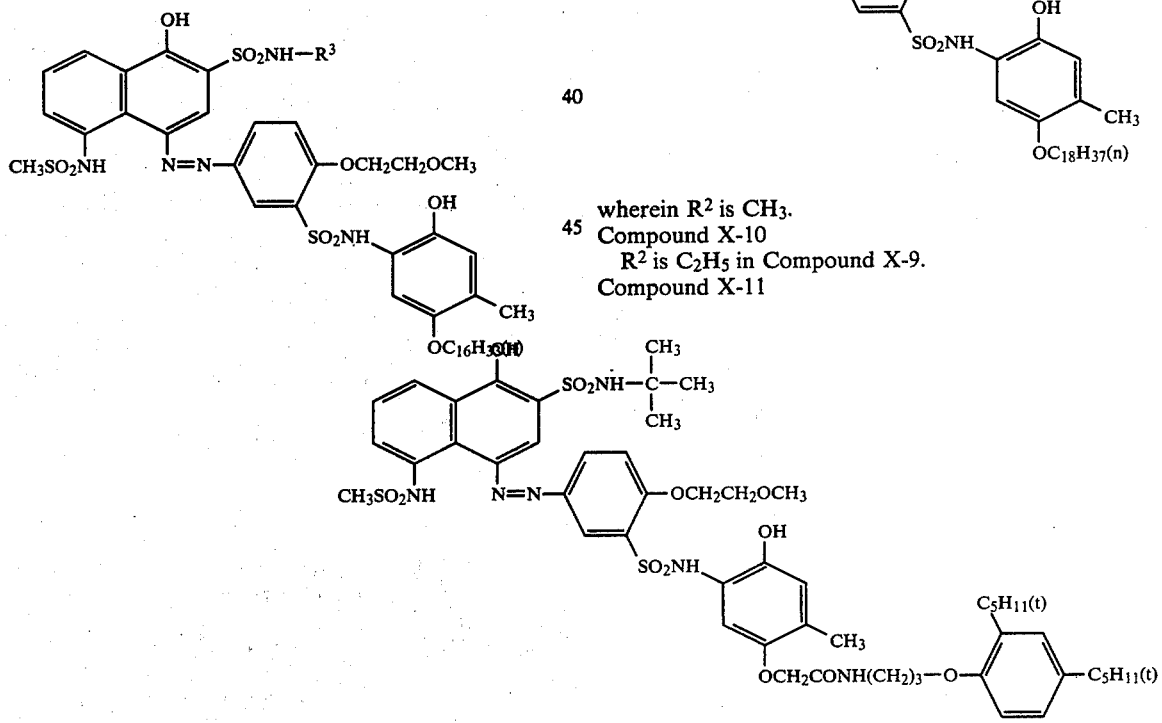
wherein $R^2$ is $CH_3$.
Compound X-10
   $R^2$ is $C_2H_5$ in Compound X-9.
Compound X-11
Compound X-12

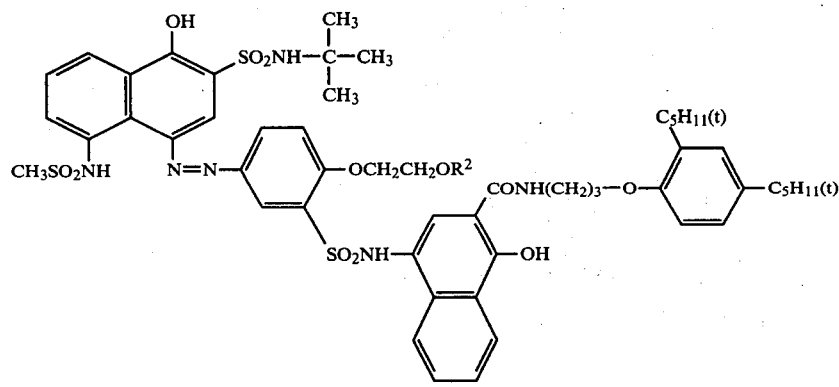
wherein R² is CH₃.
Compound X-13
R² is C₂H₅ in Compound X-12.
Compound X-14
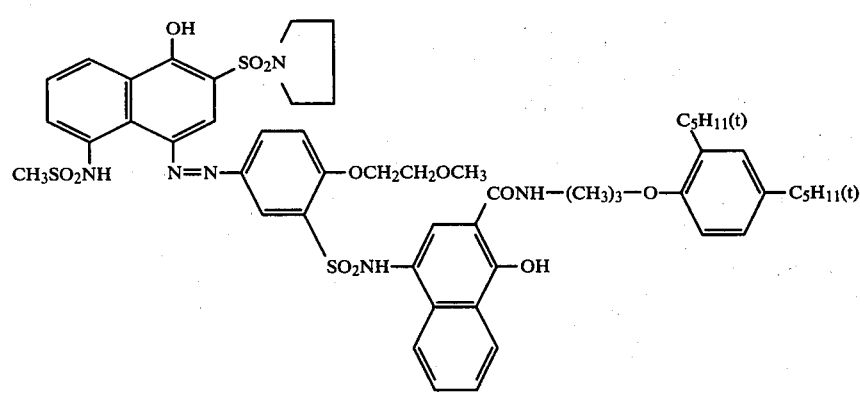
Compound X-15
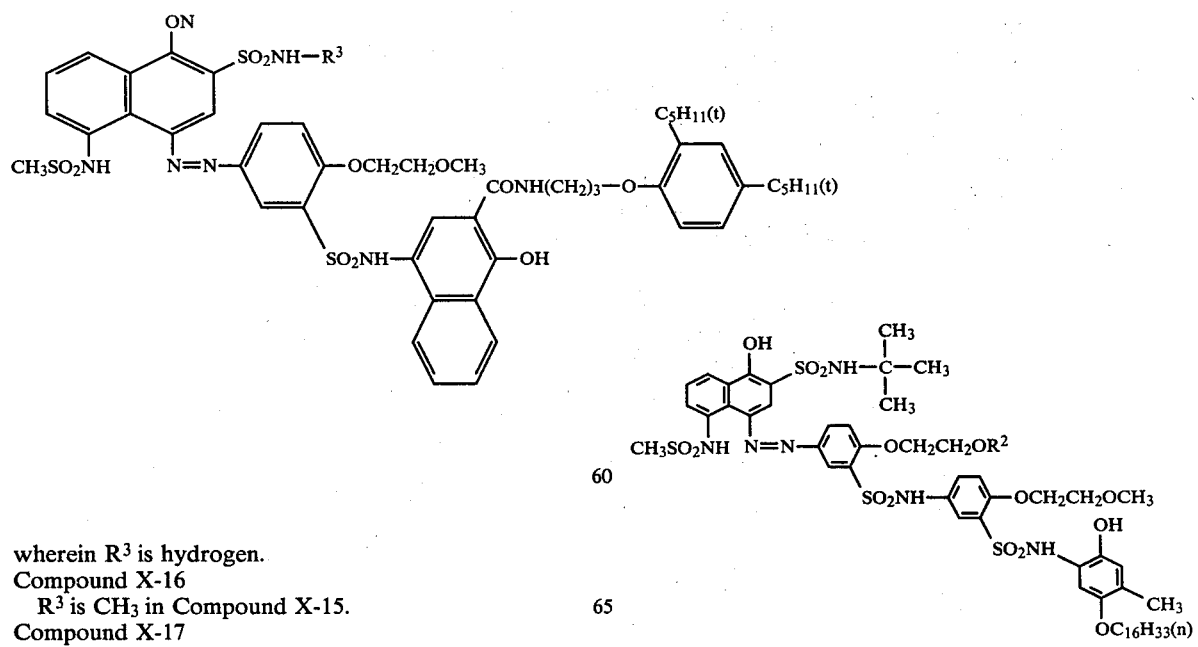
wherein R³ is hydrogen.
Compound X-16
  R³ is CH₃ in Compound X-15.
Compound X-17
  R³ is n-butyl in Compound X-15.
Compound X-18
wherein R² is CH₃.

Compound X-19
  $R^2$ is $C_2H_5$ in Compound X-18.
Compound X-20

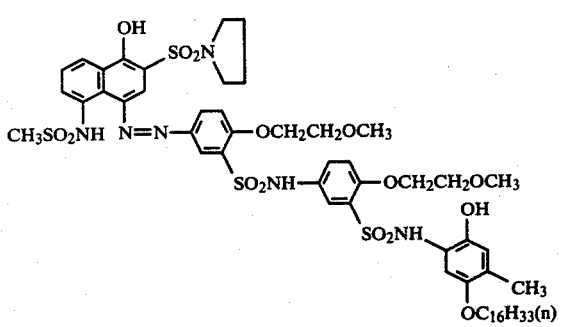

Compound X-21

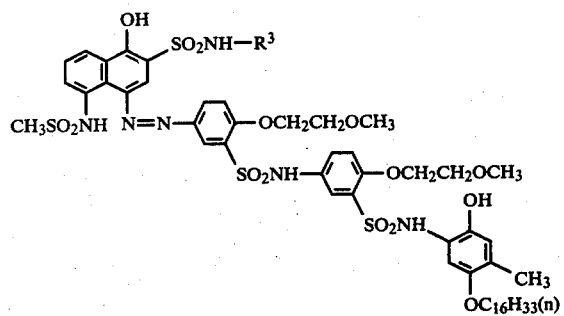

wherein $R^3$ is hydrogen.
Compound X-22
  $R^3$ is $CH_3$ in Compound X-21.
Compound X-23
  $R^3$ is n-butyl in Compound X-21.
Compound X-24

$R^3$ is $C_2H_5$ in Compound X-4.
Compound X-26
  $R^3$ is methoxyethyl in Compound X-4.
Compound X-27
  $R^3$ is isopropyl in Compound X-4.
Compound X-28

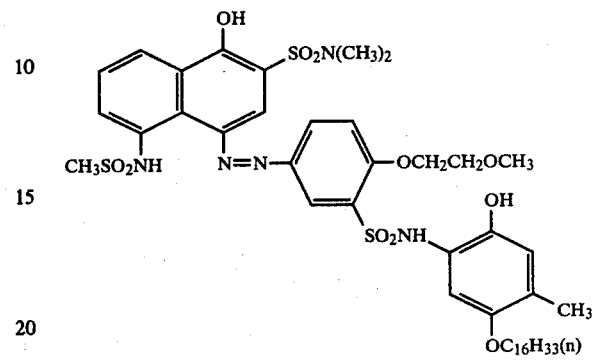

Compound X-29

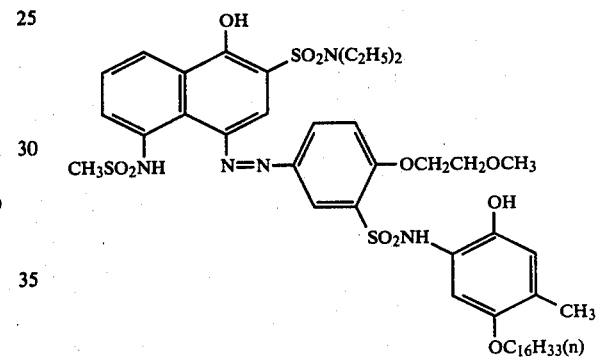

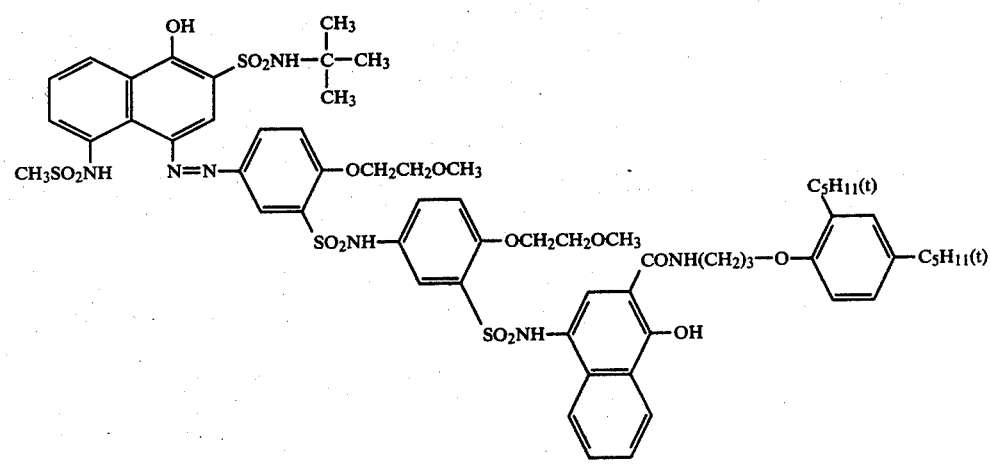

Compound X-25

The compound of the formula (X) releases a novel megenta dye compound represented by the following general formula (XI) or (XII):

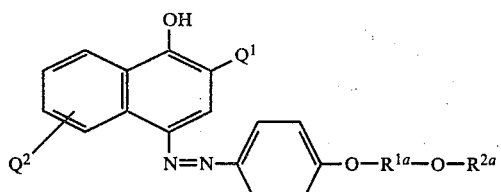

(XI)

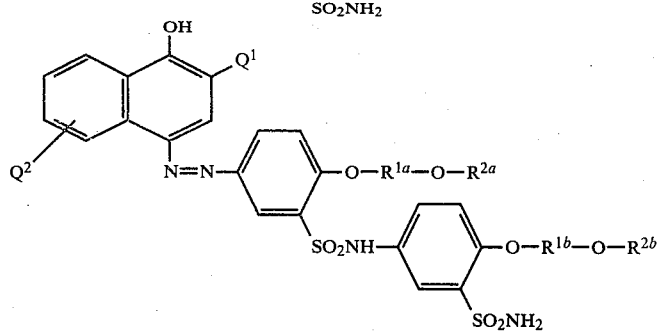

(XII)

wherein $Q^1$, $Q^2$, $R^1$ and $R^2$ each has the same meaning as defined in the general formula (X), when the compound is oxidized under alkaline conditions.

The DRR compounds derived from the intermediate of the present invention can be obtained by a condensation reaction of a sulfonyl halide of an azo dye represented by the formula (XIII) with an amine represented by the formula (XIV) or (XV):

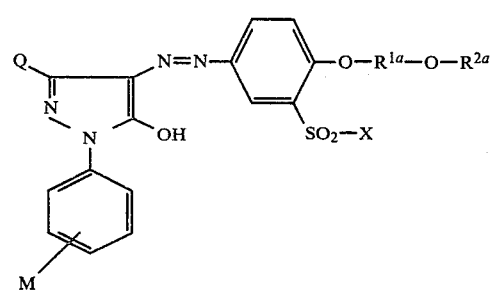

(XIII)

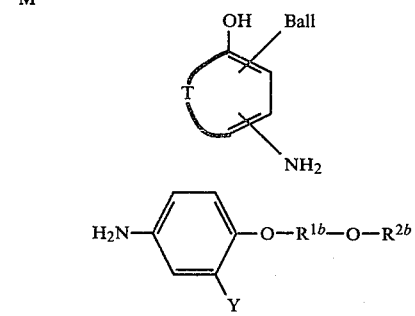

(XIV)

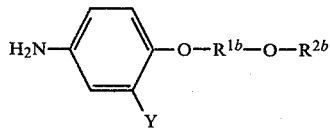

(XV)

wherein Q, M, $R^{1a}$, $R^{1b}$, $R^{2a}$ and $R^{2b}$ each has the same meaning as defined in the formula (II); T and Ball each has the same meaning as defined in the formula (III); and X represents a halogen atom (for example, a chlorine atom, a fluorine atom, etc.). The sulfonyl halide of the azo dye in turn is synthesized from the sulfonic acid of the present invention as explained below.

In general, the condensation reaction is preferably carried out in the presence of a basic compound. Examples of suitable basic compounds which can be employed include a hydroxide of an alkali metal or an alkaline earth metal (for example, sodium hydroxide, potassium hydroxide, barium hydroxide, calcium hydroxide, etc.), an aliphatic amine (for example, triethylamine, etc.), an aromatic amine (for example, N,N-diethylaniline, etc.), a heteroaromatic amine (for example, pyridine, quinoline, α-, β- or γ-picoline, lutidine, collidine, 4-(N,N-dimethylamino)pyridine, etc.), or a heterocyclic base (for example, 1,5-diazabicyclo[4,3,0-]nonene-5, 1,8-diazabicyclo[5,4,0]undecene-7, etc.). A heteroaromatic amine is particularly preferred (more preferably pyridine) of the above-described basic compounds where a compound represented by the formula (XIII) wherein X is a chlorine atom, that is, a sulfonyl chloride is used.

An azo dye represented by the formula (XVII) can be obtained by diazotizing a compound of the formula (I) of the present invention and coupling it with a compound represented by the formula (XVI), i.e., a coupler or a coupling component.

Diazotization of compound of the formula (I) can be conducted according to the methods described in, for example, Yutaka Hosoya, *Shin Senryo Kagaku* (*New Dye Chemistry*), (Gihodo, (1963)), pp. 114–120, or Hiroshi Horiguchi, *Sosetsu Gosei Senryo* (*Review on Synthetic Dyes*), (Sankyo Shuppan (1970)), pp. 114–124. Above all, it is preferable to diazotize the compound of the present invention according to a method usually called the reversal method. In this method, 1 mol of diazo component, about 1 mol of sodium nitrite and about 1 mol of sodium hydroxide (or hydroxide of other alkali or alkaline earth metal) are dissolved in water, and this mixture is added to a cooled mineral acid aqueous solution (e.g., dilute hydrochloric acid, dilute sulfuric acid, etc.). As the amounts of sodium nitrite and sodium hydroxide, the above-described amounts are preferable, though they may be added in excess amounts. The thus-obtained solution of diazonium salt is mixed with an aqueous solvent solution or aqueous solution containing about 1 mol of the compound represented by the general formula (XVI) (coupler) to conduct the coupling reaction. As the organic solvents for dissolving the coupler, water-miscible solvents are preferable. For example, alcohols (e.g., methanol, ethanol, 2-propanol, methoxyethanol, ethoxyethanol, etc.), carbonamides (e.g., N,N-dimethylacetamide, N,N-dimethylformamide, etc.), carboxylic acids (e.g., acetic acid, propionic acid, etc.) are preferable. It is also possible to dissolve the coupler in the mixture of these solvents. Further, the coupler may be used as an alkaline aqueous solution. Upon this coupling reaction, it is preferable to have a basic material present. As the preferable basic materials, there are illustrated sodium acetate, potassium acetate, sodium hydroxide, potassium hydroxide, sodium carbonate, potassium carbonate, sodium hydrogen-carbonate, etc. Details of the coupling reaction will be described hereinafter. Descriptions of the foregoing Horiguchi's book, pp. 124–129, H. E. Fierz-David and L. Blangy, *Fundamental Process of Dye Chemistry* (Interscience Publishers Inc. New York (1949)), pp. 239–297, and K. Venkataraman, *The Chemistry of Synthetic Dyes* (Academic Press Inc., New York (1952)), Chap. 11 are also instructive.

By converting a sulfonic acid group of the azo dye to a sulfonyl halide using a chlorinating agent, a compound represented by the formula (XIII) can be prepared.

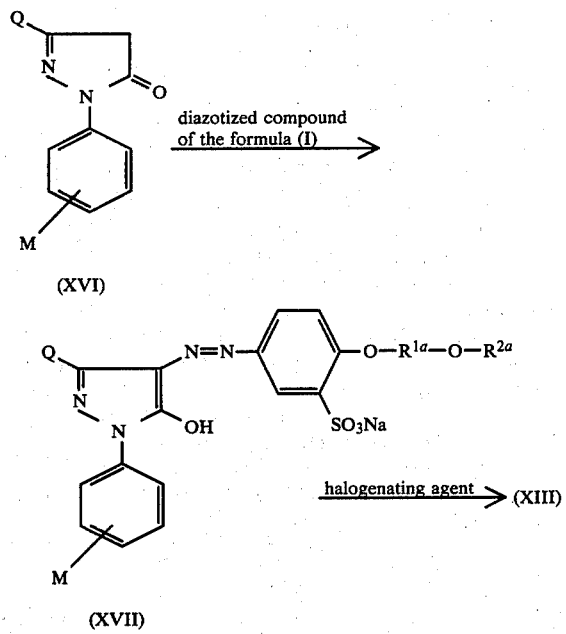

wherein Q, M, $R^{1a}$ and $R^{2a}$ each has the same meaning as defined in the formula (II).

In order to convert the compound of the formula (XVII) to a compound of the formula (XIII) wherein X is a chlorine atom, a chlorinating agent such as phosphorus oxychlorine ($POCl_3$), thionyl chloride ($SOCl_2$), or phosphorus pentachloride ($PCl_5$) is preferably used. The chlorinating reaction is preferably carried out in the presence of a carbonamide (reaction accelerator), N,N-dimethylacetamide, N,N-dimethylformamide, N-methylpyrrolidone, etc.

The necessary amount of the above-described chlorinating agent is a stoichiometric amount but, in many cases, it is desirable to use it in excess (1.5 to 50 times, preferably 1.5 to 10 times the theoretical amount). In most cases, this reaction proceeds at room temperature (about 25° C.). Where the reaction is too vigorous, it is possible to cool it to about 0° C. On the other hand, where the reaction proceeds too slowly, the reaction system may be heated within the range of 25° to 150° C. (preferably 25° to 100° C.).

Compounds wherein X represents other halogens can also be synthesized according to the method described in *Houben-Weyls Methoden der Organishen Chemie*, edited by E. Müeller, Vol. IX, pp. 557–598 (1958).

Typical examples of the amine represented by the formula (XIV) are described, for example, in U.S. Pat. Nos. 4,055,428, 3,932,380, 3,931,144 and *Research Disclosure*, Vol. 130, No. 13024.

A typical method for the preparation of the amine represented by the formula (XV) is schematically illustrated below:

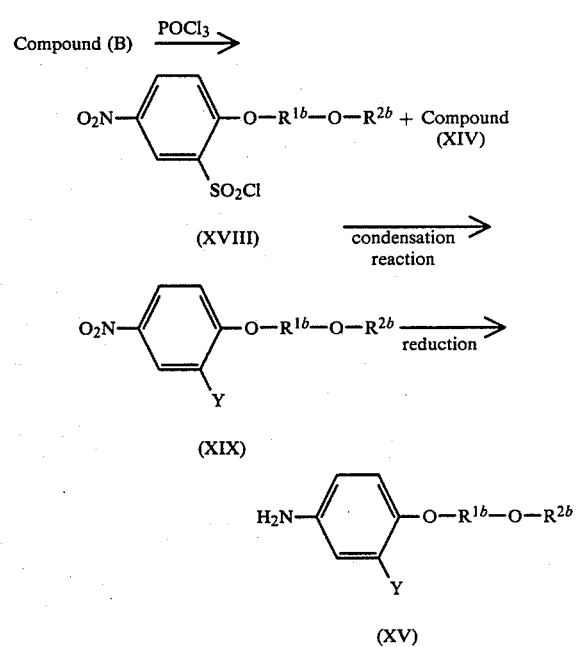

Additional examples of chlorinating agents used for obtaining a compound represented by the formula (XVIII) include those described above for the preparation of the compound of the formula (XIII) described above. In this case the reaction is also preferably carried out in the presence of N,N-dimethylacetamide, N,N-dimethylformamide, N-methylpyrrolidone, or the like.

The condensation reaction of the sulfonyl chloride represented by the formula (XVIII) and an amine represented by the formula (XIV) to obtain a compound of the formula (XIX) is preferably carried out in the presence of a basic compound, with suitable examples of basic compounds being as described with respect to the condensation reaction of the compound of the formula (XIII) with the compound of the formula (XIV) or (XV) described above.

In addition, typical examples of the reduction reactions applied for obtaining a compound represented by the formula (XV) include a reduction for the compound (B) hereinbefore described. It should be emphasized that, in the compound of the formula (XV), the basicity of the amino group is increased due to the presence of the $R^{2b}$—O—$R^{1b}$—O—group positioned to the said amino group. Accordingly, this provides an advantage that the following condensation reaction of the compound of the formula (XV) with a sulfonyl halide of the formula (XIII) proceeds easily.

A compound represented by the formula (X) can be prepared in accordance with the method described above except that an intermediate of the formula (XX) is employed in place of the intermediate of the formula (XIII):

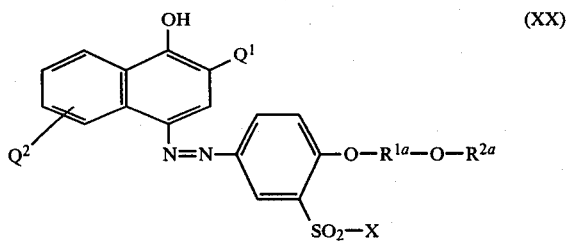

wherein $Q^1$, $Q^2$, $R^{1a}$ and $R^{2a}$ each has the same meaning as defined in the formula (X); and X has the same meaning as defined in the formula (XIII). These compounds are the subject of copending and commonly assigned Ser. No. 956,698, filed Nov. 1, 1978.

The compound of the present invention is not only useful as an intermediate for the synthesis of the DRR compounds described above, but also useful as an intermediate in the preparation of other azo dyes, and is particularly useful as a diazo component.

A specific example of the synthesis of a compound represented by the formula (II) from a compound represented by the formula (I) is illustrated below for convenience.

REFERENCE SYNTHESIS EXAMPLE 1

Synthesis of Compound II-1

(a) Synthesis of 3-cyano-4-[4-(2-methoxyethoxy)-5-sulfophenylazo]-1-phenyl-5-pyrazolone To a solution containing 8.0 g of sodium hydroxide and 200 ml of water was added 49.4 g of 5-amino-2-(2-methoxyethoxy)benzenesulfonic acid, and further 50 ml of an aqueous solution containing 13.8 g of sodium nitrite.

A solution of 400 ml of water and 60 ml of concentrated hydrochloric acid was prepared independently.

The above-described solution was added dropwise to this acidic solution while the reaction mixture was maintained at 5° C. or lower. After that, the reaction mixture was stirred at 5° C. or lower for 30 minutes to complete the reaction.

A solution containing 16.0 g of sodium hydroxide, 200 ml of water, 33.0 g of sodium acetate, and 200 ml of methanol was prepared. To the solution was added 37.0 g of 3-cyano-1-phenyl-5-pyrazolone and then added dropwise the above-described diazo solution while the reaction mixture was maintained at 10° C. or lower. After the completion of the dropwise addition, the mixture was stirred at 10° C. or lower for 30 minutes, and further stirred at room temperature for 1 hour and the crystals thus-precipitated were recovered by filtration. The crystals were washed with 200 ml of acetone and air-dried.

Yield: 52.0 g. Melting Point: 263° to 265° C.

(b) Synthesis of 3-cyano-4-[4-(2-methoxyethoxy)-5-chlorosulfonylphenylazo]-1-phenyl-5-pyrazolone 50 ml of N,N-dimethylacetamide was added dropwise at 50° C. or lower to a mixture of 51.0 g of 3-cyano-4-[4-(2-methoxyethoxy)-5-sulfophenylazo]-1-phenyl-5-pyrazolone prepared as described in Step (a) of Reference Synthesis Example 1 above, and then 250 ml of acetone and 50 ml of phosphorous oxychloride was added. After completion of the dropwise addition, the reaction mixture was stirred for about 1 hour, and was then gradually poured into 1.0 l of ice water. The crystals thus-precipitated were recovered by filtration, washed with 100 ml of acetonitrile and air-dried.

Yield: 46.7 g. Melting Point: 181° to 183° C.

(c) Synthesis of Compound II-1

To 20 ml of N,N-dimethylacetamide were added 40 g of hydrochloric acid salt of 2-amino-4-hexadecyloxy-5-methylphenol and 4.6 g of 3-cyano-4-[4-(2-methoxyethoxy)-5-chlorosulfonylazo]-1-phenyl-5-pyrazolone prepared as described in Step (b) above. 4.7 ml of pyridine was added dropwise to the reaction mixture with stirring and stirring was continued at room temperature for 2 hours. After the completion of the reaction, 30 ml of methanol and 10 ml of water were added to the reaction solution. The crystals thus-precipitated were recovered by filtration and then recrystallized from 200 ml of acetonitrile.

Yield: 5.3 g. Melting Point: 162° to 164° C.

REFERENCE SYNTHESIS EXAMPLE 2

Synthesis of Compound II-15

(a) Synthesis of 2-(2-Methoxyethoxy)-5-nitrobenzenesulfonyl chloride 59 g of sodium 2-(2-methoxyethoxy)-5-nitrobenzenesulfonate prepared as described in Synthesis Example 1 was added to a mixture of 200 ml of acetone and 75 ml of phosphorous oxychloride and 75 ml of dimethylacetamide was added dropwise to the mixture with stirring while the reaction mixture was maintained at 30° to 40° C. After completion of the dropwise addition, the reaction mixture was allowed to stand while stirring until it cooled to room temperature. The reaction mixture was then poured into 600 ml of ice water, stirred for 30 minutes and the crystals thus-precipitated were recovered by filtration. The crystals were washed with 100 ml of water and air-dired.

Yield: 56 g. Melting Point: 74° to 74.5° C.

(b) Synthesis of 2-[2-(2-Methoxyethoxy)-5-nitrobenzenesulfonamido]-4-hexadecyloxy-5-methylphenol 20 g of 2-amino-4-hexadecyloxy-5-methylphenol hydrochloride and 18 g of 2-(2-methoxyethoxy)nitrobenzene-5-sulfonyl chloride prepared as described in Step (a) above were added to a mixture of 100 ml of tetrahydrofuran and 10 ml of pyridine and the mixture was stirred at room temperature for 3 hours. The reaction mixture was added to a mixture of 300 ml of ice water and 50 ml of concentrated hydrochloric acid with stirring. The crystals thus-precipitated were recovered by filtration, washing with water, air-dired and recrystallized from 100 ml of acetonitrile.

Yield: 35 g. Melting Point: 85.5° to 86° C.

(c) Synthesis of 2-[2-(2-Methoxyethoxy)-5-aminobenzenesulfonamido]-4-hexadecyloxy-5-methylphenol 32 g of 2-[2-(2-methoxyethoxy)nitrobenzenesulfonamido]-4-hexadecyloxy-5-methylphenol, 24 g of iron powder, 12 g of $Fe_3O_4$, 0.6 g of ammonium chloride and 25 ml of water were added to 300 ml of isopropyl alcohol and the mixture was refluxed in a stream bath with stirring for 1 hour. After completion of the reaction, the mixture was filtered while hot and the filtrate was cooled with ice. The crystals thus-precipitated were recovered by filtration, washed with 50 ml of isopropyl alcohol and air-dried.

Yield: 23 g. Melting Point: 142° to 144° C.

(d) Synthesis of Compound II-15

5.9 g of 2-[2-(2-methoxyethoxy)-5-aminobenzenesulfonamido]-4-hexadecyloxy-5-methylphenol prepared as described in Step (c) and 4.6 g of 3-cyano-4-[4-(2-methoxyethoxy)-5-chlorosulfonylphenylazo]-1-phenyl-5-pyrazolone prepared as described in Step (b) of Reference Synthesis Example 1 were added to 20 ml of N,N-dimethylacetamide. 1.6 ml of pyridine was added dropwise thereto with stirring and further was allowed to stand with stirring at room temperature for 2 hours. After completion of the reaction, 30 ml of methanol and 10 ml of water were added to the reaction mixture. Crystals thus-precipitated were recovered by filtration and recrystallized from 100 ml of acetonitrile.

Yield: 8.7 g. Melting Point: 133° to 141° C.

REFERENCE SYNTHESIS EXAMPLE 3

Synthesis of Compound X-1

(a) Synthesis of 2-(N-tert-Butylsulfamoyl)-4-[4-(2-methoxyethoxy)-5-sulfophenylazo]-5-methanesulfonamido-1-naphthol To a solution containing 1.7 g of sodium hydroxide and 80 ml of water, 9.9 g of 5-amino-2-(2-methoxyethoxy)benzenesulfonic acid and then 10 ml of an aqueous solution containing 2.8 g of sodium nitrite were added. The solution was added dropwise to a solution containing 18 ml of concentrated hydrochloric acid and 70 ml of water at a temperature of 5° C. or below. The mixture was stirred for 30 minutes at 5° C. or below to complete the reaction (preparation of a diazo solution).

To a solution containing 8.0 g of sodium hydroxide, 40 ml of water and 150 ml of methyl alcohol, 14.9 g of 2-tert-butylsulfamoyl-5-methanesulfonamido-1-naphthol was added. To the solution thus-prepared, the above-described diazo solution was added dropwise at a temperature of 10° C. or below. After completion of the dropwise addition, the mixture was stirred for 30 minutes at 10° C. or below and 20 ml of concentrated hydrochloric acid was added thereto. The crystals thus-preciptated were collected by filtration, washed with 200 ml of acetone and air-dried.

Yield: 19 g. Melting Point: 215° to 220° C.

(b) Synthesis of 2-(N-tert-Butylsulfamoyl)-4-[4-(2-methoxyethoxy)-5-chlorosulfonylphenylazo]-5-methanesulfonamido-1-naphthol To a mixed solution containing 19 g of 2-(N-tert-butylsulfamoyl)-4-[4-(2-methoxyethoxy)-5-sulfophenylazo]-5-methanesulfonamido-1-naphthol prepared as described in Step (a) above, 100 ml of acetone and 20 ml of phosphorous oxychloride, 20 ml of N,N-dimethylacetamide was added dropwise at a temperature of 50° C. or below. After completion of the dropwise addition, the mixture was stirred for 1 hour and was poured gradually into 500 ml of ice water. The crystals thus-precipitated were collected by filtration, washed with 50 ml of acetonitrile and air-dried.

Yield: 14 g. Melting Point: 148° to 153° C.

(c) Synthesis of Compound X-1

To 40 ml of N,N-dimethylacetamide, 20 g of 2-amino-4-hexadecyloxy-5-methylphenol hydrochloride and 13 g of 2-(N-tert-butylsulfamoyl)-4-[4-(2-methoxyethoxy)-5-chlorosulfonylphenylazo]-5-methanesulfonamido-1-naphthol prepared as described in Step (b) above were added. 10 ml of pyridine was added dropwise to the mixture with stirring and the mixture was stirred at room temperature for 2 hours. The reaction mixture was poured into 200 ml of ice water containing 10 ml of hydrochloric acid. The crystals thus-precipitated were collected by filtration, washed with water, air-dried and recrystallized from 50 ml of methyl alcohol.

Yield: 5.0 g. Melting Point: 140° to 142° C.

REFERENCE SYNTHESIS EXAMPLE 4

Synthesis of Compound X-3

(a) Synthesis of 2-(1-Pyrrolidinylsulfonyl)-4-[4-(2-methoxyethoxy)-5-sulfophenylazo]-5-methanesulfonamido-1-naphthol To a solution containing 0.9 g of sodium hydroxide and 40 ml of water, 4.9 g of 5-amino-2-(2-methoxyethoxy)benzenesulfonic acid and then a solution containing 1.4 g of sodium nitrite and 5 ml of water were added. The above-described solution was added dropwise to a solution containing 9 ml of concentrated hydrochloric acid and 36 ml of ice water at a temperature of 5° C. or below. After that, the mixture was stirred for 30 minutes at 5° C. or below to complete the reaction (preparation of a diazo solution).

To a solution containing 4.0 g of sodium hydroxide, 20 ml of water and methyl alcohol, 7.4 g of 2-(1-pyrrolidinylsulfamoyl)-5-methanesulfonamido-1-naphthol was added. To the solution thus-prepared, the above-described diazo solution was added dropwise at a temperature of 10° C. or below. After completion of the dropwise addition, the mixture was stirred for 30 minutes and 10 ml of concentrated hydrochloric acid was added thereto. The crystals thus-precipitated were collected by filtration, washed with 100 ml of acetone and air-dried.

Yield: 8.7 g. Melting Point: above 250° C.

(b) Synthesis of 2-(1-Pyrrolidinylsulfonyl)-4-[4-(2-methoxyethoxy)-5-chlorosulfonylphenylazo]-5-methanesulfonamido-1-naphthol To a solution containing 8.7 g of 2-(1-pyrrolidinylsulfamoyl)-4-[4-(2-methoxyethoxy)-5-sulfophenylazo]-5-methanesulfonamido-1-naphthol prepared as described in Step (a) above, 40 ml of acetone and 9 ml of phosphorous oxychloride, 9 ml of N,N-dimethylacetamido was added dropwise at a temperature of 50° C. or below. After completion of the dropwise addition, the mixture was stirred for 1 hour at room temperature and was poured into 200 ml of ice water. The crystals thus-precipitated were collected by filtration and washed with 20 ml of acetonitrile.

Yield: 5.0 g. Melting Point: 184° to 187° C.

(c) Synthesis of Compound X-3

To 20 ml of N,N-dimethylacetamide, 3.1 g of 2-amino-4-hexadecyloxy-5-methylphenol hydrochloride and 5.0 g of 2-(1-pyrrolidinosulfamoyl)-4-[4-(2-methoxyethoxy)-5-sulfochlorophenylazo]-5-methanesulfonamido-1-naphthol prepared as described in Step (b) above were mixed. 3.6 ml of pyridine was added dropwise to the mixture with stirring and the mixture was stirred at room temperature for 2 hours. After completion of the reaction, 30 ml of methanol and 10 ml of water were added to the reaction solution, washed with 50 ml of methanol, air-dried and recrystallized from 50 ml of acetonitrile.

Yield: 4.0 g. Melting Point: 105° to 108° C.

REFERENCE EXAMPLE 1

20 mg of Dye Compound II-A represented by the following formula:

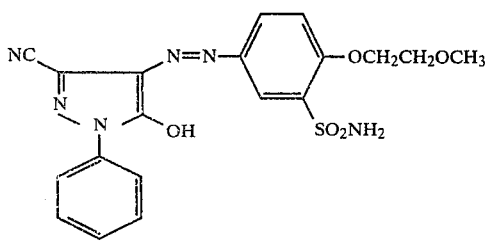

which is released from Compound II-1 was dissolved in 5.0 ml of 1/10 N aqueous solution of sodium hydroxide.

Onto a polyethylene terephthalate transparent support were coated a mordanting layer containing 3.0 g/m² of a mordant having the recurring unit shown below:

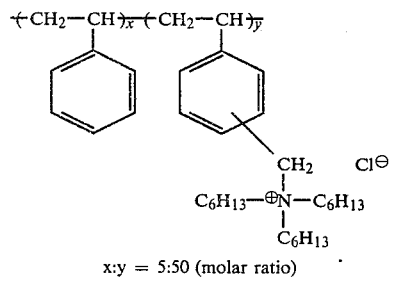

x:y = 5:50 (molar ratio)

and 3.0 g/m² of gelatin and the film was cut into strips to prepare mordanting strips. The mordanting strips were dipped in the above-described solution containing the Dye Compound II-A and dyed in order that the light-absorbance of the mordanting strips at the maximum absorption wavelength amounted to about 0.5 to about 1.0.

An absorption wavelength in the visible region of each of the dyed strips was then measured while each of the strips was dipped into buffer solutions having a variety of pH.

In the same procedure as described above, mordanting strips dyed with Dye Compound II-B represented by the following formula:

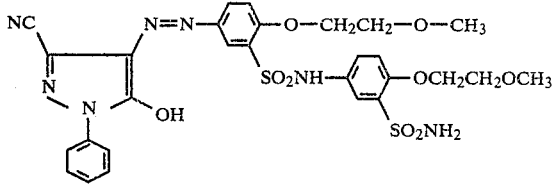

which is released from Compound II-15 were prepared and the absorption wavelength in the visible region of the mordanting strips was measured at a variety of pH.

For comparison, the absorption wavelength in the visible region was measured at a variety of pH in the same procedure as described above with respect to comparison compounds II-C and II-D below.

Comparison Compound II-C

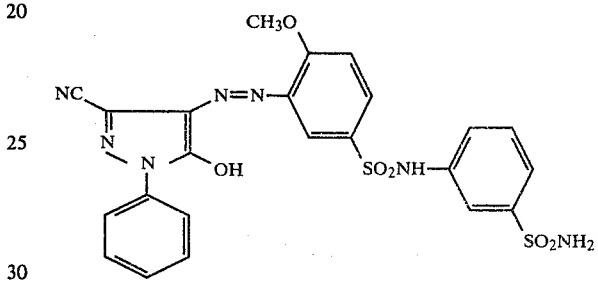

This dye compound is released by a compound disclosed in Example 1 of U.S. Pat. No. 4,013,633.

Comparison Compound II-D

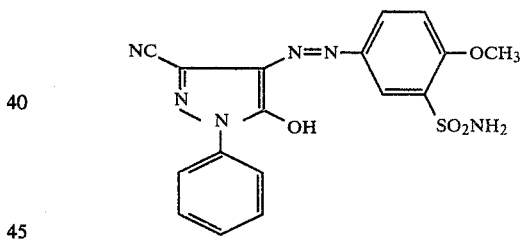

The absorption wavelength in the visible region of the dye compound which is derived from an intermediate of the present invention hardly changes over a relatively wide pH range of from about 9.2 to about 4.5. On the other hand, it was observed that the absorption wavelength of the comparison compound II-C shifts to much longer wavelengths at a pH of 5 or less. In addition, it was observed that the absorption wavelength in the visible region of the comparison compound II-D changes drastically in the pH region between 9.18 and 6.86.

The pH in a photographic unit used in the diffusion transfer process changes drastically from a high pH of about 10 or higher immediately after spreading the processing liquid to a low pH after neutralization by means of the acidic polymer layer. Accordingly, where compounds whose absorption wavelength in the visible region changes in these pH ranges such as the above-described comparison compounds II-C and II-D are employed, a color image having an excellent color reproduction cannot be formed since the color hue of the image changes with the pH of the photographic unit within a relatively short time after exposure upon development of the photographic unit. As a result, these prior art compounds are less advantageous because they do not provide the characteristics required of instant photography, that is, a photograph can be viewed immediately after the exposure to light. On the other hand, a dye compound derived from the DRR compounds prepared from the intermediate of the present invention provides a color image having excellent color reproduction, since the color hue of the dye compound does not change even with the lapse of a relatively short time after exposure. Accordingly, the dye compound derived from the compound of the present invention is very suitable for instant photography.

The difference in effect between the $CH_3OCH_2CH_2O-$ group of the above-described compound II-A and the $CH_3O-$ group of the comparison compound II-D is neither described in nor taught by prior art patents. Although there are various hypothesis for this difference, one possible reason is that the pesence of an intramolecular hydrogen bond as shown in the formula below suppresses dissociation of the $-SO_2NH-$ group.

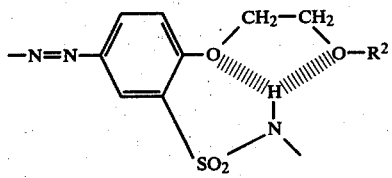

It is believed that there is no change in the absorption wavelength in the visible region of the compound II-A and the compound II-B because dissociation of the $-SO_2NH-$ group is suppressed. As a result, it is believed that the presence of two oxygen atoms positioned such that an intramolecular hydrogen bond as described above can be formed is an important aspect of the $R^2-O-R^1-O-$ group.

REFERENCE EXAMPLE 2

On a polyethylene terephthalate transparent support were coated the layers described below in the order listed to prepared four kinds of light-sensitive sheets A to D.

In the formulation described below, values in the parenthesis are the coating amount and in particular $g/m^2$ unless the unit thereof is implicitly indicated.

(1) mordanting layer containing the same mordant as used in Reference Example 1 (3.0) and gelatin (3.0).

(2) white reflecting layer containing titanium oxide (20.0) and gelatin (2.0).

(3) light-shielding layer containing carbon black (2.7) and gelatin (2.7).

(4) a layer containing N,N-diethyllaurylamide (0.20), 2,5-di-t-octylhydroquinone (0.018), gelatin (1.0) and the yellow dye releasing redox compound in the amount as described below.
Light-sensitive sheet A: Compound II-1 (0.60)
Light-sensitive sheet B: Compound II-15 (0.78)
Light-sensitive sheet C: Comparison Compound E (0.75)
Comparison Compound E

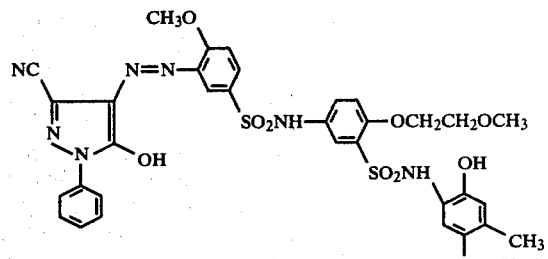

Light-sensitive sheet D    Comparison Compound F (0.75)

Comparison Compound F

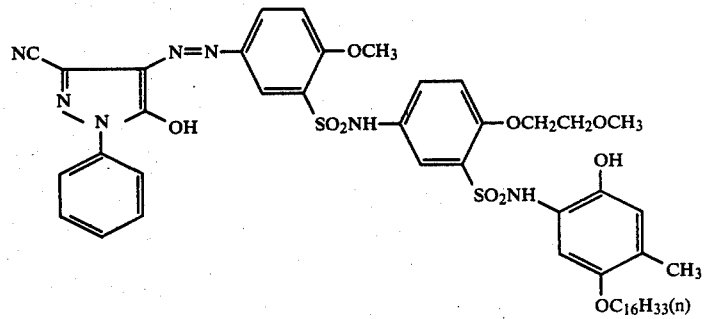

(5) a layer containing a blue-sensitive internal latent image type direct-positive silver bromide emulsion which is prepared as described in U.S. Pat. No. 3,761,276 (composition: silver amount: 1.4 g/m²; gelatin: 1.0 g/m²), sodium 5-pentadecylhydroquinone-2-sulfonate (0.11), and 1-formyl-2-{4-[3-(3-phenylthioureido)benzamido]phenyl}hydrazid (11.5 mg/mol of Ag)

(6) a layer containing gelatin (0.7).

The above-described light-sensitive sheets A to D were processed in combination with elements as described below, respectively.

| Composition of processing solution | |
|---|---|
| 4-Hydroxymethyl-4-methyl-1-phenyl-3-pyrazolidinone | 13 g |
| Methylhydroquinone | 0.18 g |
| 5-Methylbenzotriazole | 4 g |
| Sodium sulfite (anhydrate) | 1 g |
| Sodium salt of carboxymethylcellulose | 45 g |
| Carbon black | 150 g |
| Potassium hydroxide | 56 g |
| Water to make | 1 kg |

Cover Sheet

On a polyethylene terephthalate transparent support were coated layers as described below to prepare a cover sheet.

(1) acidic polymer layer comprising a coating of polyacrylic acid (a 10 wt% of aqueous solution having viscosity of about 1,000 cp; 15 g/m²).

(2) neutralization timing layer comprising a coating of 3.8 g/m² of acetyl cellulose (acetylation degree: 39.6%) and 0.2 g/m² of a styrene-maleic acid anhydride copolymer (composition: styrene:maleic anhydride=about 60:40 (molar ratio); molecular weight: about 50,000).

Processing step

The above-described cover sheet was superimposed on the above-described light-sensitive sheet. Exposure was performed through a color test chart from the cover sheet side. Then, the processing solution described above was spread between both sheets in a thickness of 70 μm. The spreading was performed with assitance of a pressure roller. The processing was carried out at 25° C. The reflection density of the images formed in the image-receiving layer was measured through the support of the light-sensitive sheet using a Macbeth reflection densitometer two hours after the processing.

The results thus-obtained are shown in Table 1.

Measurement of Transferability of Dye

Using the same technique as the processing step described above, a processing solution was spread between a light-sensitive sheet and a cover sheet. The density of the dye transferred in the image-receiving layer was measured through the support of the light-sensitive sheet using a Macbeth densitometer. The time required for obtaining 50% and 80% of the maximum density thus attained was determined based on the results of the measurement. The results thus-obtained are shown in Table 1.

Measurement of Light-Stability

Using the same technique as the processing step described above, a processing solution was spread between a light-sensitive sheet and a cover sheet. The cover sheet was stripped from the light-sensitive sheet two hours after the processing. The light-sensitive sheet was dried and then exposed to light of 17,000 lux for 7 days using a fluorescent lamp fading tester. The light fastness ratio of the color image was determined on the basis of the color image density observed before to light divided by the color image density observed after exposure to light. The results thus-obtained are shown in Table 1.

TABLE 1

| Light-Sensitive Sheet | $D_{max}$ | $D_{min}$ | Transferability 50% (sec) | 80% (sec) | Light Stability (Light Fastness Ratio) | Remarks |
|---|---|---|---|---|---|---|
| A | 1.78 | 0.22 | 48 | 180 | 0.83 | Invention |
| B | 1.76 | 0.21 | 69 | 210 | 0.80 | Invention |
| C | 1.80 | 0.21 | 87 | 258 | 0.72 | Comparison |
| D | 1.82 | 0.23 | 82 | 245 | 0.82 | Comparison |

It is apparent from the results shown in Table 1 that dye compounds derived from the intermediate of the present invention have excellent transferability.

REFERENCE EXAMPLE 3

On a polyethylene terephthalate transparent support were successively coated layers as described below to prepare three kinds of light-sensitive sheets E to G.

(1) a layer containing a green-sensitive silver iodobromide emulsion (composition: iodide (I) mol%: 3.5%, silver amount: 2.4 g/m², gelatin: 1.7 g/m²), 0.20 g/m² of diethyllauryl amide, 0.018 g/m² of 2,5-di-t-octylhydroquinone, 1.0 g/m² of gelatin and a yellow dye releasing redox compound in the amount described below:
Light-sensitive sheet E: Compound II-15 (0.78 g/m²)
Light-sensitive sheet F: Comparison Compound E (0.75 g/m²)
Light-sensitive sheet G: Comparison Compound F (0.75 g/m²)

(2) a layer containing gelatin (0.70 g/m²).

A processing was performed as described above by combining light-sensitive sheets E to G with the elements described below.

Processing Solution

| Component | A (g) | B (g) |
|---|---|---|
| 4-Hydroxymethyl-4-methyl-1-phenyl-3-pyrazolidinone | 13 | 13 |
| 5-Methylbenzotriazole | 4 | 4 |
| Sodium nitrite (anhydrate) | 1 | 1 |
| Potassium hydroxide | 56 | 22.4 |
| Sodium salt of carboxymethyl cellulose | 60 | 60 |
| Water to make up to | 1 kg | 1 kg |

Image Receiving Sheet

The mordanting sheet described in Example 1 was used as an image-receiving sheet.

Processing Step

The above-described image-receiving sheet was superimposed on the above-described light-sensitive sheet. Exposure was performed through a color test chart from the image-receiving sheet side. Then, the processing solutions A and B described above were each spread between the sheets in a thickness of 70 μm with assistance of a pressure roller. The processing was carried out at 25° C. The image-receiving sheet was stripped from the light-sensitive sheet 5 minutes after processing. The light-sensitive sheet was subjected to post processing including steps of stopping, fixing and washing.

The density of dye images transferred in the image receiving sheet was measured using a Macbeth transmittance densitometer. On the other hand, the amount of silver developed on the light-sensitive sheet was measured using an X-ray fluorescent analyser. The results thus-obtained are shown in Table 2 as the density of transferred image corresponding to the same amount of developed silver.

TABLE 2

| Relationship between the amount of developed silver and the density of transferred image | | | | | | | |
|---|---|---|---|---|---|---|---|
| Light-Sensitive Sheet | Density of Transferred Image | | | | | | Remarks |
| | Processing A | | | Processing B | | | |
| | 0.15* | 0.30* | 0.45* | 0.15* | 0.30* | 0.45* | |
| E | 0.70 | 0.83 | 0.87 | 0.38 | 0.62 | 0.70 | Invention |
| F | 0.54 | 0.60 | 0.60 | 0.30 | 0.41 | 0.47 | Comparison |
| G | 0.62 | 0.78 | 0.80 | 0.36 | 0.58 | 0.63 | Comparison |

*Amount of developed silver: g/m²

It is apparent from the results shown in Table 2 that the DRR compounds derived from the intermediate of the present invention give a higher transferred image density on the basis of the same amount of developed silver. This means that high $D_{max}$ can be obtained thereby using less silver halide.

REFERENCE EXAMPLE 4

On a polyethylene terephthalate transparent support were successively coated layers as described below to prepare light-sensitive sheet H.

(1) mordanting layer (the same as in Example 2)
(2) white reflecting layer (the same as in Example 2)
(3) light shielding layer (the same as in Example 2)
(4) a layer containing 0.58 g/m² of the cyan dye-releasing redox compound described below, 0.13 g/m² of diethyllaurylamide, 0.008 g/m² of 2,5-di-t-butylhydroquinone and 1.0 g/m² of gelatin.

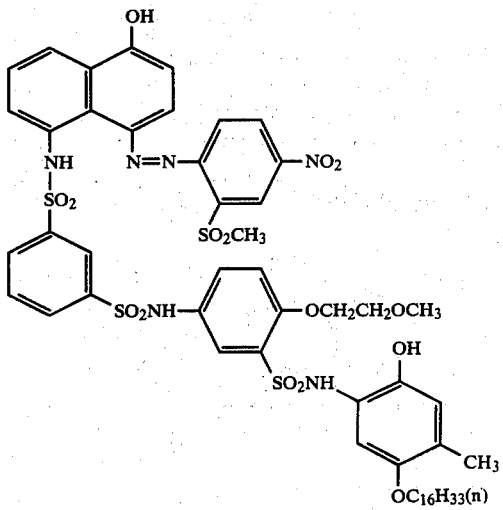

(5) a layer containing a red-sensitive internal latent image type direct-positive silver bromide emulsion prepared by a method disclosed in U.S. Pat. No. 3,716,276 (silver amount: 1.9 g/m²; and gelatin: 1.4 g/m²), 0.13 g/m² of sodium 5-pentadecylhydroquinone-2-sulfonate and 18 mg per mol of Ag of 1-formyl-2-{4-[3-(3-phenyl-thioureido)benzamido]phenyl}hydrazide.

(6) a layer containing 2.6 g/m² of gelatin and 1.0 g/m² of 2,5-dioctylhydroquinone.

(7) a layer containing 0.65 g/m² of the magenta dye-releasing redox compound described below, 0.16 g/m² of diethyllaurylamide, 0.011 g/m² of 2,5-di-t-butylhydroquinone and 1.2 g/m² of gelatin.

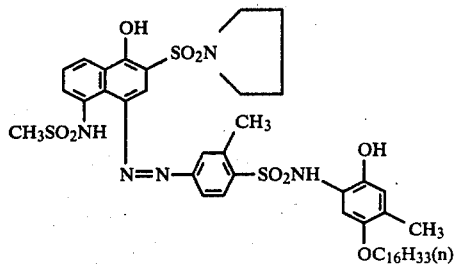

(8) a layer containing a green-sensitive internal latent image type direct-positive silver bromide emulsion prepared by a method disclosed in U.S. Pat. No. 3,716,276 (silver amount: 1.5 g/m²; and gelatin: 1.2 g/m²), 0.12 g/m² of sodium 5-pentadecylhydroquinone-2-sulfonate, and 15 mg per mol of Ag of 1-formyl-{4-[3-(3-phenyl-thioureido)benzamido]phenol}hydrazide.

(9) same as layer (6) described above.

(10) same layer as layer (4) described in Example 2 except containing the yellow dye-releasing redox compound described below which is identical to the compound disclosed in U.S. Pat. No. 3,928,312.

(11) same as layer (5) described in Example 2.

(12) a layer containing 0.70 g/m² of gelatin.

In addition, light-sensitive sheets I, J, K and L were prepared using the compounds described below in place of the yellow dye-releasing redox compound incorporated in the above-described layer (10), respectively.

Light-sensitive sheet I: Comparison Compound E

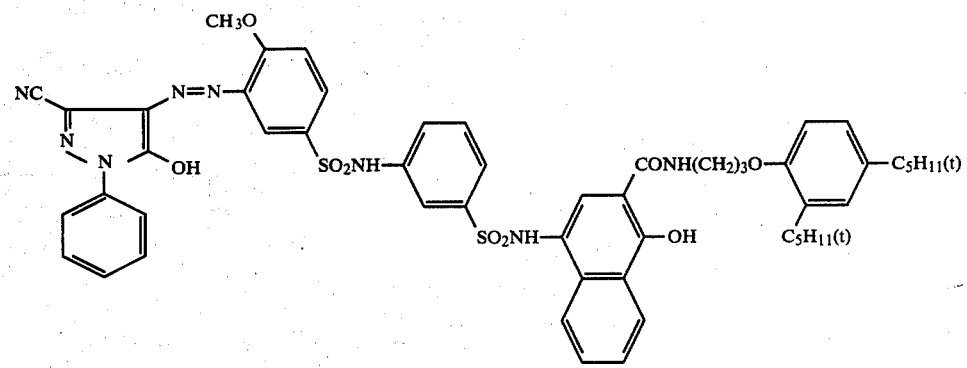

Light-sensitive sheet J: Comparison Compound F
Light-sensitive sheet K: Compound II-1
Light-sensitive sheet L: Compound II-9

Processing Solution

The same processing solution as used in Example 2.

Cover Sheet

On a polyethylene terephthalate transparent support were successively coated layers described below to prepare a cover sheet.

(1) polymer acid layer containing 20 g/m² of an acrylic acid·butyl acrylate copolymer (composition: acrylic acid:butyl acrylate=about 80:about 20 (molar ratio); and average molecular weight: 50,000) and 0.42 g/m² of 5-(2-cyanoethylthio)-1-phenyltetrazole.

(2) neutralization timing layer containing 5.6 g/m² of acetyl cellulose (acetylization degree: 39.6%) and 0.36 g/m² of a styrene-maleic anhydride copolymer (composition: styrene:maleic anhydride=about 60:about 40 (molar ratio), and molecular weight: 50,000).

(3) a layer containing 3.3 g/m² of a styrene-butyl acrylate-acrylic acid (molar ratio of polymerization 52:42:6).

Processing Step

The above-described cover sheet was superimposed on the above-described light-sensitive sheet and was imagewise exposed to light through a continuous tone wedge from the cover sheet side. Then, the above-described processing was spread between both sheets in a thickness of 78 μm. Spreading was performed with the assistance of a pair of juxtaposed pressure-applying rollers. The processing was carried out at 25° C. The density of transferred dye images was measured two hours after the processing. Satisfactory dye images were obtained in each of light-sensitive sheets. The results thus-obtained are shown in Table 3.

Measurement of Transferability of Dye

The transferability of dye released from a yellow dye-releasing redox compound was measured in accordance with the method described in Example 2. The results thus-obtained are shown in Table 3.

TABLE 3

| Light-Sensitive Sheet | $D_{max}$* Obtained | Time Required for Obtaining 50% of $D_{max}$ | Time Required for Obtaining 80% of $D_{max}$ | Remarks |
|---|---|---|---|---|
| H | 1.82 | 3 min 24 sec | 10 min 30 sec | Comparison |
| I | 1.80 | 4 min 6 sec | 12 min 7 sec | Comparison |
| J | 1.90 | 3 min 39 sec | 16 min 15 sec | Comparison |
| K | 1.84 | 2 min 20 sec | 8 min 7 sec | Invention |
| L | 1.80 | 2 min 5 sec | 7 min 55 sec | Invention |

*The $D_{max}$ is the yellow dye density observed through a blue filter.

It is apparent from the results shown in Table 3 that dye compounds derived from the intermediate of the present invention have an excellent transferability.

REFERENCE EXAMPLE 5

Dye compound X-A represented by the following formula:

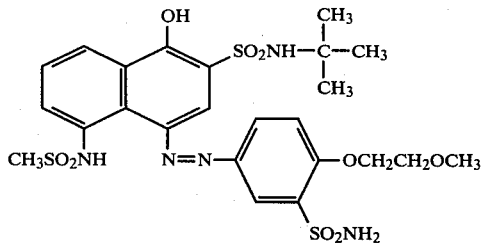

which is released from Compound X-1 was dissolved in N,N-dimethylformamide (DMF) to prepare a $10^{-3}$ M solution. 0.25 ml of the solution was diluted with 11.5 ml of DMF. Then, a mixture of 1.25 ml of a $10^{-1}$ M solution of butylacrylate and 12.5 ml of a buffer having a pH of 5.05 (Britton-Robinson Buffer) was added thereto. The solution was allowed to stand at room temperature (25° to 29° C.) and the decrease of absorbance at a maximum absorption wavelength in a visible region was measured. The remaining rate of Dye Compound X-A was determined from the value thus measured. In addition, assuming that the decrease in the remaining rate can be shown by a pseudo first order equation, a reaction rate constant of the pseudo first order reaction, i.e., K was determined.

In the same manner as described above, the remaining rate of dye and K were determined with respect to Dye Compound X-B respected by the following formula:

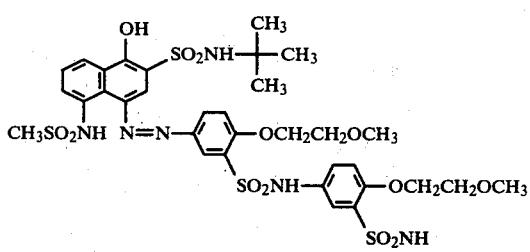

which is released from Compound X-18.

For comparison, the remaining rate of dye and K were determined in the same manner described above with respect to comparison compounds X-C, X-D and X-E below:

Comparison Compound X-C

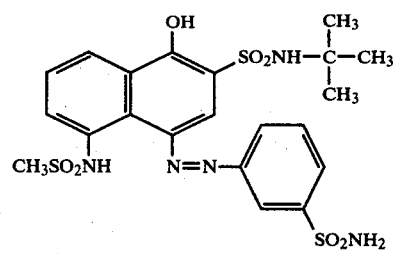

Comparison Compound X-D

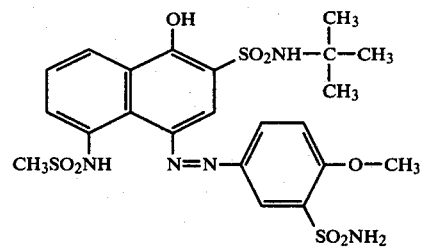

Comparison Compound X-E

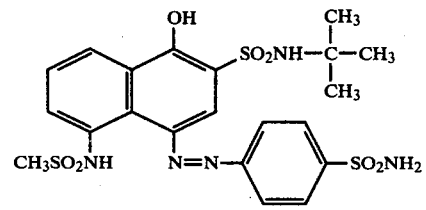

The results thus-obtained are shown in Table 4.

TABLE 4

| Reaction of Released Dye Compound with Butylacrylate | |
|---|---|
| Compound | K (day$^{-1}$) |
| X-A | 0.027 |
| X-B | 0.023 |
| X-C | 0.072 |
| X-D | 0.048 |

TABLE 4-continued

Reaction of Released Dye
Compound with Butylacrylate

| Compound | K (day$^{-1}$) |
|---|---|
| X-E | 0.098 |

It is apparent from the results shown in Table 4 that Compounds X-A and X-B each has a remarkably small value of K, that is, a remarkably excellent light fastness in comparison with Comparison Compounds X-C, X-D and X-E.

While the invention has been described in detail and with reference to specific embodiments thereof, it will be apparent to one skilled in the art that various changes and modifications can be made therein without departing from the spirit and scope thereof.

What is claimed is:

1. A compound of the formula:

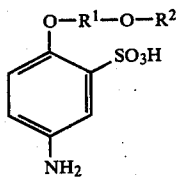 (I)

wherein $R^1$ represents an alkylene group having 2 or more carbon atoms and $R^2$ represents an alkyl group provided that the two oxygen atoms in the $-O-R^1-O-R^2$ moiety are not connected to the same carbon atom in $R^1$.

2. The compound of claim 1, wherein $R^1$ represents a straight chain or branched chain alkylene group having 2 to 8 carbon atoms.

3. The compound of claim 2, wherein $R^1$ is a group selected from the group consisting of a straight chain alkylene group of the formula $-(CH_2)_p-$, wherein p is an integer of 2 to 4 and a branched chain alkylene group having 3 or 4 carbon atoms.

4. The compound of claim 3, wherein $R^1$ is $-CH_2CH_2-$.

5. The compound of claim 1, wherein $R^2$ represents a straight chain or branched chain alkyl group having 1 to 8 carbon atoms.

6. The compound of claim 5, wherein $R^2$ represents a straight chain or branched chain alkyl group having 1 to 4 carbon atoms.

7. The compound of claim 1, wherein $R^1$ is $-CH_2-CH_2-$ and $R^2$ represents a straight chain or branched chain alkyl group having 1 to 4 carbon atoms.

8. The compound of claim 1, wherein $R^1$ is $-CH_2-CH_2-$ and $R^2$ represents a straight alkyl group having 1 to 4 carbon atoms.

9. The compound of claim 1, wherein $R^1$ is $-CH_2-CH_2-$ and $R^2$ is a methyl group or an ethyl group.

* * * * *